(12) United States Patent
Breuer et al.

(10) Patent No.: US 11,541,149 B2
(45) Date of Patent: Jan. 3, 2023

(54) SYSTEMS AND METHODS FOR OPTIMIZED PATIENT SPECIFIC TISSUE ENGINEERING VASCULAR GRAFTS

(71) Applicant: Research Institute at Nationwide Children's Hospital, Columbus, OH (US)

(72) Inventors: Christopher Breuer, New Albany, OH (US); Cameron Best, Blacklick, OH (US); Robert Strouse, Columbus, OH (US); Narutoshi Hibino, Towson, MD (US); Yong Ung-Lee, Columbus, OH (US)

(73) Assignee: Research Institute at Nationwide Children's Hospital, Columbus, OH (US)

( * ) Notice: Subject to any disclaimer, the term of this patent is extended or adjusted under 35 U.S.C. 154(b) by 162 days.

(21) Appl. No.: 15/781,679

(22) PCT Filed: Dec. 12, 2016

(86) PCT No.: PCT/US2016/066204
§ 371 (c)(1),
(2) Date: Jun. 5, 2018

(87) PCT Pub. No.: WO2017/100782
PCT Pub. Date: Jun. 15, 2017

(65) Prior Publication Data
US 2018/0353649 A1 Dec. 13, 2018

Related U.S. Application Data

(60) Provisional application No. 62/309,285, filed on Mar. 16, 2016, provisional application No. 62/266,309, filed on Dec. 11, 2015.

(51) Int. Cl.
| | | |
|---|---|---|
| *A61L 27/38* | (2006.01) | |
| *A61L 27/18* | (2006.01) | |
| *A61L 27/20* | (2006.01) | |
| *A61L 27/24* | (2006.01) | |
| *A61L 27/50* | (2006.01) | |
| *D01D 5/00* | (2006.01) | |
| *B33Y 10/00* | (2015.01) | |
| *B33Y 80/00* | (2015.01) | |
| *A61L 27/54* | (2006.01) | |
| *A61L 27/58* | (2006.01) | |

(52) U.S. Cl.
CPC .......... *A61L 27/3834* (2013.01); *A61L 27/18* (2013.01); *A61L 27/20* (2013.01); *A61L 27/24* (2013.01); *A61L 27/507* (2013.01); *A61L 27/54* (2013.01); *A61L 27/58* (2013.01); *B33Y 10/00* (2014.12); *B33Y 80/00* (2014.12); *D01D 5/0076* (2013.01); *A61L 2300/41* (2013.01); *A61L 2300/414* (2013.01); *A61L 2300/416* (2013.01)

(58) Field of Classification Search
CPC ............. A61L 27/18; A61L 2300/41; A61L 2300/414; A61L 2300/416; A61L 27/20; A61L 27/24; A61L 27/3834; A61L 27/507; A61L 27/54; A61L 27/58; C08L 67/04; C08L 77/00; C08L 85/02; B33Y 10/00; B33Y 80/00; D01D 5/0076
See application file for complete search history.

(56) References Cited

U.S. PATENT DOCUMENTS

| | | |
|---|---|---|
| 5,459,128 A | 10/1995 | Rollins |
| 5,716,394 A | 2/1998 | Bruchman |
| 5,891,108 A | 4/1999 | Leone |
| 5,922,554 A | 7/1999 | Fielding |
| 6,441,004 B1 | 8/2002 | Faull |
| 6,517,858 B1 | 2/2003 | Le Moel |
| 6,833,387 B1 | 12/2004 | Faull |
| 6,918,929 B2 | 7/2005 | Udipi |
| 6,923,828 B1 | 8/2005 | Wiktor |
| 6,945,992 B2 | 9/2005 | Goodson |
| 6,986,785 B2 | 1/2006 | O'Shaughnessy |
| 7,060,090 B2 | 6/2006 | Thornton |
| 7,144,419 B2 | 12/2006 | Cheng |
| 7,163,555 B2 | 1/2007 | Dinh |

(Continued)

FOREIGN PATENT DOCUMENTS

| | | |
|---|---|---|
| CA | 2540382 | 4/2005 |
| EA | 011822 | 2/2007 |

(Continued)

OTHER PUBLICATIONS

American Heritage, "Definition of Patency", Medical Dictionary, Houghton Mifflin Co., (2004).

(Continued)

*Primary Examiner* — Blaine Lankford
(74) *Attorney, Agent, or Firm* — Pabst Patent Group LLP

(57) ABSTRACT

It has been established that optimizing cell seeding onto tissue engineering vascular grafts (TEVG) is associated with reduced inflammatory responses and reduced post-operative stenosis of TEVG. Cell seeding increased TEVG patency in a dose dependent manner, and TEVG patency improved when more cells were seeded, however duration of incubation time showed minimal effect on TEVG patency. Methods of engineering patient specific TEVG including optimal numbers of cells to maintain graft patency and reduce post-operative stenosis are provided. Closed, single-use customizable systems for seeding TEVG are also provided. Preferably the systems are custom-designed based on morphology of the patient specific graft, to enhance the efficacy of cell seeding.

22 Claims, 15 Drawing Sheets

(56) References Cited

U.S. PATENT DOCUMENTS

| | | |
|---|---|---|
| 7,323,008 B2 | 1/2008 | Kantor |
| 7,482,434 B2 | 1/2009 | Gudas |
| 7,611,532 B2 | 11/2009 | Bates |
| 7,651,527 B2 | 1/2010 | Krivoruchko |
| 7,655,034 B2 | 2/2010 | Mitchell |
| 7,678,141 B2 | 3/2010 | Greenan |
| 7,744,645 B2 | 6/2010 | Thornton |
| 7,942,917 B2 | 5/2011 | Nowak |
| 8,001,925 B2 | 8/2011 | Kantor |
| 8,034,099 B2 | 10/2011 | Pellegrini |
| 8,048,149 B2 | 11/2011 | Yang |
| 8,066,760 B2 | 11/2011 | Mitchell |
| 8,100,960 B2 | 1/2012 | Bruszewski |
| 8,157,855 B2 | 4/2012 | Eidenschink |
| 8,172,893 B2 | 5/2012 | Moore |
| 8,182,524 B2 | 5/2012 | Spiridigliozzi |
| 8,187,284 B2 | 5/2012 | Jordan |
| 8,187,322 B2 | 5/2012 | Smith |
| 8,197,528 B2 | 6/2012 | Colgan |
| 8,206,432 B2 | 6/2012 | Kveen |
| 8,221,490 B2 | 7/2012 | Keeen |
| 8,231,669 B2 | 7/2012 | Miller |
| 8,236,044 B2 | 8/2012 | Robaina |
| 8,252,048 B2 | 8/2012 | Smith |
| 8,252,065 B2 | 8/2012 | Ward |
| 8,257,425 B2 | 9/2012 | Davidson |
| 8,257,431 B2 | 9/2012 | Henderson |
| 8,292,945 B2 | 10/2012 | Welsh |
| 8,298,278 B2 | 10/2012 | Gregorich |
| 8,298,280 B2 | 10/2012 | Yadin |
| 8,348,991 B2 | 1/2013 | Weber |
| 8,348,992 B2 | 1/2013 | Brown |
| 8,348,993 B2 | 1/2013 | Tischler |
| 8,353,952 B2 | 1/2013 | Thompson |
| 8,359,998 B2 | 1/2013 | Shekalim |
| 8,361,140 B2 | 1/2013 | Meyer |
| 8,372,134 B2 | 2/2013 | Schlick |
| 8,372,138 B2 | 2/2013 | Jordan |
| 8,377,112 B2 | 2/2013 | Griffin |
| 8,388,676 B2 | 3/2013 | Stinson |
| 8,398,695 B2 | 3/2013 | Chalekian |
| 8,414,637 B2 | 4/2013 | Chouinard |
| 8,414,639 B2 | 4/2013 | Tischler |
| 8,414,656 B2 | 4/2013 | Davoudi |
| 9,090,863 B2 | 7/2015 | Breuer |
| 2002/0125613 A1 | 9/2002 | Cominsky |
| 2002/0187184 A1 | 12/2002 | Golomb |
| 2003/0013686 A1 | 1/2003 | Golomb |
| 2003/0064965 A1 | 4/2003 | Richter |
| 2003/0082148 A1 | 5/2003 | Ludwig |
| 2003/0136860 A1 | 7/2003 | Hurley |
| 2004/0044405 A1 | 3/2004 | Wolff |
| 2004/0063654 A1 | 4/2004 | Davis |
| 2004/0071861 A1 | 4/2004 | Mandrusov |
| 2005/0058692 A1 | 3/2005 | Hai-Quan |
| 2005/0120951 A1 | 6/2005 | Spencer |
| 2005/0124534 A1 | 6/2005 | Noble |
| 2005/0143817 A1 | 6/2005 | Hunter |
| 2005/0163821 A1 | 7/2005 | Sung |
| 2005/0220848 A1 | 10/2005 | Bates |
| 2006/0045905 A1 | 3/2006 | Ozeki |
| 2006/0217437 A1 | 9/2006 | Burmester |
| 2007/0014102 A1 | 1/2007 | Drane |
| 2007/0141042 A1 | 6/2007 | Franano |
| 2008/0091234 A1 | 4/2008 | Kladakis |
| 2008/0097575 A1 | 4/2008 | Cottone |
| 2009/0012607 A1 | 1/2009 | Kim |
| 2009/0043378 A1 | 2/2009 | Cheng |
| 2009/0054350 A1 | 2/2009 | Tayot |
| 2009/0069368 A1 | 3/2009 | Bono |
| 2009/0098183 A1 | 4/2009 | Detamore |
| 2010/0092534 A1 | 4/2010 | Hezi-Yamit |
| 2010/0129414 A1 | 5/2010 | Dolan |
| 2010/0292773 A1 | 11/2010 | Schmid |
| 2010/0303889 A1 | 12/2010 | Breuer |
| 2011/0281358 A1 | 11/2011 | Breuer |
| 2013/0013083 A1 | 1/2013 | Blum |
| 2013/0022328 A1 | 1/2013 | Gronvall |
| 2014/0072951 A1 | 3/2014 | Johnson |
| 2014/0147484 A1 | 5/2014 | Breuer |
| 2014/0272225 A1 | 9/2014 | Johnson |
| 2014/0358217 A1 | 12/2014 | Stankus |
| 2016/0136326 A1 | 5/2016 | Fisher |

FOREIGN PATENT DOCUMENTS

| | | |
|---|---|---|
| EA | 200600470 | 2/2007 |
| EP | 1066378 | 1/2001 |
| RU | 2452517 | 3/2011 |
| RU | 2440128 | 1/2012 |
| WO | 1997028262 | 8/1997 |
| WO | 1998045413 | 10/1998 |
| WO | 9951741 | 10/1999 |
| WO | 199951741 | 10/1999 |
| WO | 2000012497 | 3/2000 |
| WO | 2000061576 | 10/2000 |
| WO | 01010421 | 2/2001 |
| WO | 2001010421 | 2/2001 |
| WO | 2002102432 | 12/2002 |
| WO | 2004016606 | 2/2004 |
| WO | 2004050659 | 6/2004 |
| WO | 2004080982 | 9/2004 |
| WO | 2004112710 | 12/2004 |
| WO | 2005013915 | 2/2005 |
| WO | 2005063965 | 7/2005 |
| WO | 05094914 | 10/2005 |
| WO | 2006026306 | 3/2006 |
| WO | 2006099332 | 9/2006 |
| WO | 2007059253 | 5/2007 |
| WO | 2008009062 | 1/2008 |
| WO | 2008047198 | 4/2008 |
| WO | 2009089324 | 7/2009 |
| WO | 2011146046 | 11/2011 |
| WO | 2014197790 | 12/2014 |
| WO | 2015168674 | 11/2015 |

OTHER PUBLICATIONS

Burgess, et al., "A concanavalin A-like lectin domain in the CHS1/LYST protein, shared by members of the Beach family", Bioinformatics, 25(10):1219-1222 (2009).

Haliotis, et al., "Chédiak-Higashi gene in humans I. Impairment of natural-killer function", J. Exp. Med., 151:1039-48 (1980).

Jay, et al., "Engineering of multifunctional gels integrating highly efficient growth factor delivery with endothelial cell transplantation", Faseb J., 22:2949-2956 (2008).

Stacy, et al., "Targeted imaging of matrix metalloproteinase activity in the evaluation of remodeling tissue-engineered vascular grafts implanted in a growing lamb model", Journal of Thoracic and Cardiovascular Surgery, 148(5):2227-2233 (2014).

Lee, et al., "Rational design of an improved tissue-engineered vascular graft: determining the optimal cell dose and incubation time", Regenerative Medicine, 11(2):159-167 (2016).

Levitsy, et al., "Sirolimus and paclitaxel—main conclusions from implanting stents with antiproliferative coatings", Theses of Second Russian session of interventional cardiologists, (2005).

Kurobe, et al., "Comparison of the Biological Equivalence of Two Methods for Isolating Bone Marrow Mononuclear Cells for Fabricating Tissue-Engineered Vascular Grafts", Tissue Eng Part C, 21(6):597-604 (2015).

Alexi-Meskishvili, et al., "Optimal conduit size for extracardiac Fontan operation", Eur. J. Cardiothorac. Surg., 18:690-5 (2000).

American Heritage Medical Dictionary, "Definition of Patency", Medical dictionary, Houghton Mifflin Co, (2004).

Arras, et al., "Monocyte activation in angiogenesis and collateral growth in the rabbit hindlimb", J Clin Invest, 101(1):40-50 (1998).

Barrat, et al., "Genetic and physical mapping of the Chediak-Higashi syndrome on chromosome 1q42-43", Am. J. Hum. Genet, 59:625-32 (1996).

(56) References Cited

OTHER PUBLICATIONS

Battler and Brenner, "Liver fibrosis", J Clin Invest., 115:209-18 (2005).
Bauters, et al., "The biology of restenosis", Prog. Cardiovasc. Dis., 40:107-16 (1997).
Bermudez, et al., "Late results of the peel operation for replacement of failing extracardiac conduits", Ann. Thorac. Surg., 77:881-8 (2004).
Bitterman and Henke, "Fibroproliferative disorders", Chest, 99(3):81s-4s (1991).
Brennan, et al., "Tissue-engineered vascular grafts demonstrate evidence of growth and development when implanted in a juvenile animal model", Annals of Surgery, 248(3):370-377 (2008).
Chandrasekar, et al., "Platelets and restenosis", J Am College Cardiology, 35(3):555-62 (2000).
Cheng, et al., "Role of macrophages in restricting herpes simplex virus type 1 growth after ocular infection", Invest Opthalmol. Vis. Sci., 41:1402-1409 (2000).
Cho, et al., "Enhancement of in vivo endothelialization of tissue-engineered vascular grafts by granulocyte colony-stimulation factor", J Biomed Mater Res., 76(2):252-63 (2006).
Cleveland, et al., "Failure of cryopreserved homograft valved conduits in the pulmonary circulation, Circulation", 86(suppl II):II150-3 (1992).
Clowes, et al., "Significance of quiescent smooth muscle migration in the injured rat carotid artery", Circ. Res., 56:139-145 (1985).
Conte, "The ideal small arterial substitute: a search for the Holy Grail", Faseb, 12:43-5 (1998).
Costa and Simon, "Molecular basis of restenosis and drug-eluting stents", Circulation, 111(17):2257-2273 (2005).
Cotran, et al., "Cytokine-endothelial interactions in inflammation, immunity, and vascular injury", J Am Soc Nephrol., 1:225-35 (1990).
De Zelicourt, et al., "Imaging and patient-specific simulations for the Fontan surgery: current methodologies and clinical applications", Prog Pediatr Cardiol; 30:31-44 (2010).
Dearani, et al., "Late follow-up of 1095 patients undergoing operation for complex congenital heart disease utilizing pulmonary ventricle to pulmonary artery conduits", Ann. Thorac. Surg., 75:399-411 (2003).
Di Lorenzo, et al., "Akt1 is critical for acute inflammation and histamine-mediated vascular leakage", PNAS, 106:14552-7 (2009).
Duncan, et al., "Challenges in translating vacular tissue engineering to the pediatric clinic", Vasc. Cell, 3(1):23 (2011).
Duncan, et al., "TGFβR1 inhibition blocks the formation of stenosis in tissue-engineered vascular grafts", J Am Coll Cardiol., 65(5):512-4 (2015).
Espinosa-Heidmann, et al., "Macrophage depletion diminishes lesion size and severity in experimental choroidal neovascularization", Invest. Ophthalmol. Vis. Sci., 44:3586-3592 (2003).
Fahmy, et al., "Surface modification of biodegradable polyesters with fatty acid conjugates for improved drug targeting", Biomaterials, 26:5727-5736 (2005).
Fernandez, et al., "Biological and engineering design considerations for vascular tissue engineered blood vessels (TEBVs)", Current opinion in chemical engineering, 3:83-90 (2014).
Ferrera, et al., "Recombinant renewable polyclonal antibodies", mAbs, 7(1):32-41 (2015).
Fingerle, et al., "Role of platelets in smooth muscle cell proliferation and migration after vascular injury in rat carotid artery", PNAS, 86:8412-6 (1989).
Fontan and Baudet, "Surgical repair of tricuspid atresia", Thorax, 26(3):240-8 (1971).
Fontan, et al., "Outcome after a "perfect" Fontan operation", Circulation, 81:1520-36 (1990).
Frank, et al., "Caveolin-1 and caveolae in atherosclerosis: differential roles in fatty streak formation and neointimal hyperplasia", Curr. Opin. Lipidol., 15:523-9 (2004).
Fu, et al., "SM16, an orally active TGF-beta type I receptor inhibitor prevents myofibroblast induction and vascular fibrosis in the rat carotid injury model", Arterioscler Thromb. Vasc. Biol., 28(4):665-671 (2008).
Geissmann et al., "Development of monocytes, macrophages, and dendritic cells", Science 327:656-61 (2010).
Giannico, et al., "Clinical outcome of 193 extracardiac Fontan patients: the first 15 years", J. Amer. College Card., 47(10):2065-73 (2006).
Glagov, "Intimal hyperplasia, vascular modeling, and the restenosis problem", Circulation, 89:2888-91 (1994).
Gordon and Taylor, "Monocyte and macrophage heterogeneity", Nat. Rev. Immunol. 5:953-64 (2005).
Gotoh, et al., "Tyrosine phosphorylation sites on FRS2alpha responsible for Shp2 recruitment are critical for induction of lens and retina", PNAS, 101(49):17144-9 (2004).
Gragerov, et al., "Large-scale, saturating insertional mutagenesis of the mouse genome", PNAS, 104(36):14406-11 (2007).
Gribbin, et al., "Incidence and mortality of idiopathic pulmonary fibrosis and sarcoidosis in the UK", Thorax, 61:980-5 (2006).
Hager, et al., "Long-term survival of patients with univentricular heart not treated surgically" J. Thorac. Cardiovasc. Surg., 123:1214-7 (2002).
Hagihara, et al., "Vascular protection by chloroquine during brain tumor therapy with Tf-CRM107", Cancer Research, 60(2):230-234 (2000).
Haliotis, et al., "Chédiak-Higashi gene in humans I. Impairment of natural-killer function", Journal of Experimental Medicine, 151:1039-1048 (1980).
Hibino, et al., "A critical role for macrophages in neovessel formation and the development of stenosis in tissue-engineered vascular grafts", Faseb J. 25(12):4253-63 (2011b).
Hibino, et al., "Late-term results of tissue-engineered vascular grafts in humans", J Thorac Cardiovasc Surg. 139(2), 431-436.e432 (2010).
Hibino, et al., "Tissue-engineered vascular grafts form neovessels that arise from regeneration of the adjacent blood vessel", FASB, 25(8):2731-9 (2011a).
Homann, et al., "Reconstruction of the RVOT with valved biological conduits: 25 years experience with allografts and xenografts", Eur. J. Cardiothorac. Surg., 17:624-30 (2000).
Huang and Ogawa, "Fibroproliferative disorders and their mechanobiology", Connect Tissue Res., 53(3):187-96 (2012).
Information Hyperlinked Over Proteins, "CCL2 Vhemokine (C-C motif) ligand 2", http://www.ihop-net.org/UnPub/iHOP/gismo/92036.hmtl?Organism_ID=1,accessed Aug. 10, 2012.
International Search Report for PCT application PCT/US2015/029014 dated Sep. 15, 2015.
International Search Report for PCT application PCT/US2016/066204 dated Mar. 10, 2014.
Isomatsu, et al. "Extracardiac total cavopulmonary connection using a tissue-engineered graft", J. Thorac. Cardiovasc. Surg. 126(6):1958-62 (2003).
Itoh and Ornitz, et al., "Evolution of the Fgf and Fgfr gene families", Trends in Genet., 20(11):563-9 (2004).
Jay, et al., "Nanoparticles containing anti-inflammatory agents as chemotherapy adjuvants: optimization and in vitro characterization", Faseb Jour., 10(1):133-40 (2008).
Jonas, et al., "Long-term follow-up of patients with synthetic right heart conduits", Circulation, 72(suppl II):II77-83 (1985).
Kakisis, et al., Artificial blood vessel: the Holy Grail of peripheral vascular surgery J. Vasc. Surg., 41:349-54 (2005).
Karamlou, et al., Oversizing pulmonary homograft conduits does not significantly decrease allograft failure in children, Eur. J. Cardiothorac. Surg., 27:548-53 (2005).
Khurana, et al., "Angiogenesis-dependent and independent phases of intimal hyperplasia", Circulation., 110(16):2436-43 (2004).
Kinlay, et al., "Endothelial function and coronary artery disease", Curr. Opin. Lipidol., 12:383 (2001).
Krauss, et al., "Multi-organ, multi-lineage engraflment by a single bone marrow-derived stem cell", Cell, 105:369-77 (2001).

(56) References Cited

OTHER PUBLICATIONS

Kurobe, et al., "Comparison of a closed system to a standard open technique for preparing tissue-engineered vascular grafts", Tissue Eng Part C Methods 21(1), 88-93 (2015).
Langer and Vacanti, "Tissue engineering", Science, 260:920-6 (1993).
Lardo, et al., "Fluid dynamic comparison of intra-atrial and extracardiac total cavopulmonary connections", J. Thorac. Cardiovasc. Surg., 117:697-704 (1999).
Lee, et al., "TGF-β receptor 1 inhibition prevents stenosis of tissue-engineered vascular grafts by reducing host mononuclear phagocyte activation", FASB, 30:2627-36 (2016).
Lee, et al.m "Implantation of inferior vena cava interposition graft in mouse model.", J Vis Exp. (88) doi: 10.3791/51632 (2014).
Lin, et al., "Generation of an Frs2alpha conditional null allele", Genesis. 45(9):554-9 (2007).
Malavaud, et al., "Direct FGF receptor 1 activation through an anti-idiotypic strategy mimicks the biological activity of FGF-2 and inhibits the progression of the bladder carcinoma derived from NBT-II cells", Oncogene, 23:6769-78 (2004).
Mantovani, et al., "Macrophage polarization: tumor-associated macrophages as a paradigm for polarized M2 mononuclear phagocytes", Trends Immunol., 23: 549-55 (2002).
Mashkovsky, "Medications", Medicine, 12(2):404-407 (1993).
Mathiowitz, et al., "Polyanhydride Microspheres as Drug Carriers: Microencapsulation by Solvent Removal", J. Appl. Polymer Sci., 35:755-774 (1988).
Mathiowitz, et al.,"Novel Microcapsules for Delivery Systems", Reactive Polymers, 6:275-83 (1987).
Matsumura, et al., "Evaluation of tissue-engineered vascular autografts", Tissue Eng., 12:3075-83 (2006).
Matsumura, et al., "First evidence that bone marrow cells contribute to the construction of tissue-engineered vascular autografts in vivo", Circulation, 108(14):1729-34 (2003b).
Matsumura, et al., "Successful application of tissue engineered vascular autografts , Clinical experience", Biomaterials, 24:2303-8 (2003).
Mcallister, et al. "Effectiveness of haemodialysis access with an autologous tissue-engineered vascular graft: a multicentre cohort study", Lancet 373(9673), 1440-6 (2009).
Melchiorri, et al., "3D-Printed Biodegradable Polymeric Vascular Grafts", Adv Healthc Mater. 5(3):319-25 2015).
Mirensky, et al., "Tissue-engineered vascular grafts: does cell seeding matter?", J Ped Surg., 45(6):1299-1305 (2010).
Mizumoto, et al., "Enhanced contact hypersensitivity in human monocycle chemoattractant protein-1 transgenic mouse", Immunology, 204(4):477 (2001) Abstract only.
Mood, et al., "SNT1/FRS2 mediates germinal vesicle breakdown induced by an activated FGF receptor1 in Xenopus oocytes", J Biol Chem., 277(36):33196-204 (2002).
Murakami , et al., "The FGF system has a key role in regulating vascular integrity", J Clin Invest. 118(10):3355-66 (2008).
Murakami, et al., "Activated protein C prevents LPS-induced pulmonary vascular injury by inhibiting cytokine production", Am J Physiol Lung Cell Mol Physiol., 272:L197-L202 (1997).
Naito, et al., "Successful clinical application of tissue-engineered graft for extracardiac Fontan operation", J. Thorac. Cardiovasc. Surg., 125:419-20 (2003).
Ohtani, et al., "Blockade of vascular endothelial growth factor suppresses experimental restenosis after intraluminal injury by inhibiting recruitment of monocyte lineage cells", Circulation., 110(16):2444-52 (2004).
Olson, et al., "Mortality from pulmonary fibrosis increased in the United States from 1992 to 2003." Am J Respir Crit Care Med. 176:277-84 (2007).
Ovroutski, et al., "Comparison of somatic development and status of conduit after extracardiac Fontan operation in young and older children", Eur. J. Cardiothorac. Surg., 26:1073-9 (2004).
Owida, et al., "Artery vessel fabrication using the combined fused deposition modeling and electrospinning techniques", Rapid Prototyping Journal, 17(1):37 (2011).
Park, et al., "EW-7203, a novel small molecule inhibitor of transforming growth factor-β (TGF-β) type I receptor/activin receptor-like kinase-5, blocks TGF-β1-mediated epithelial-to-mesenchymal transition in mammary epithelial cells", Cancer Sci., 102(10):1889-96 (2011).
Partovian , et al., "Syndecan-4 regulates subcellular localization of mTOR Complex2 and Akt activation in a PKCalpha-dependent manner in endothelial cells", Mol Cell, 32(1):140-9 (2008).
Patterson, et al.m "Tissue-engineered vascular grafts for use in the treatment of congenital heart disease: from the bench to the clinic and back again", Regenerative Medicine 7(3), 409-419 (2012).
Petrossian, et al., "Early results of the extracadiac conduit fontan operation", J. Thorac. Cardiovasc. Surg., 117:688-96 (1999).
Petrossian, et al., "The extracardiac conduit Fontan operation using minimal approach extracorporeal circulation: early and midterm outcomes", J. Thorac. Cardiovasc. Surg., 132:1054-63 (2006).
Poh, et al., "Blood vessels engineered from human cells", Lancet, 365:2122-24 (2005).
Raghavan, et al., "Toward a biomechanical tool to evaluate rupture potential of abdominal aortic aneurysm: identification of a finite strain constitutive model and evaluation of its applicability", J Biomech, 33:475-482 (2000).
Restrepo, et al., "Hemodynamic Impact of Superior Vena Cava Placement in the Y-Graft Fontan Connection", Ann Thorac Surg. 101:183-9 (2016).
Reumaux, et al., "Priming by tumor necrosis factor-alpha of human neutrophil NADPH-oxidase activity induced by anti-proteinase-3 or anti-myeloperoxidase antibodies", J Leukoc Biol., 80:1424-33 (2006).
Robinson, et al., "A constitutively active and nuclear form of the MAP kinase ERK2 is sufficient for neurite outgrowth and cell transformation", Curr Biol., 8(21):1141-50 (1998).
Rocco, et al., "In vivo applications of electrospun tissue-engineered vascular grafts: a review", Tissue Eng Part B Rev.. 20:628-640 (2014).
Rogers and Holen,, et al., "Tumour macrophages as potential targets of bisphosphonates", J Transl Med., 9:177 (2011).
Roh, et al., "Construction of an autologous tissue-engineered venous conduit from bone marrow-derived vascular cells: optimization of cell harvest and seeding techniques", Journal of Pediatric Surgery, 42(1):198-202 (2007).
Roh, et al., "Tissue-engineered vascular grafts transform into mature blood vessels via an inflammation-mediated process of vascular remodeling", PNAS, 107(10):4669-74 (2010).
Roh, et al.m "Small-diameter biodegradable scaffolds for functional vascular tissue engineering in the mouse model", Biomaterials. 29(10):1454-63 (2008).
Rudnic, "Oral solid dosage forms", Remington's Pharmaceutical Sciences, (21st Ed.):889-964 (2005).
Saito, et al., "A biodegradable polymer as a cytokine delivery system for inducing bone formationNature", Biotechnology, 19(4):332-335 (2001).
Samanek, "Children with congenital heart disease: probability of natural survival", Pediatr. Cardiol., 13:152-8 (1992).
Schiller, et al., "Participation of macrophages in atherosclerotic lesion morphology in LDLr-/-mice", Journal of Lipid Research, 45:1398-1409 (2004).
Seedial, et al., Local drug delivery to prevent restenosis J Vasc Surg., 57(5):1403-14 (2013).
Shinoka, et al., "Creation of viable pulmonary artery autografts through tissue engineering", J. Thorac. Cardiovasc. Surg., 115:536-46 (1998).
Shinoka, et al., "Midterm clinical result of tissue-engineered vascular autografts seeded with autologous bone marrow cells", J. Thorac. Cardiovasc. Surg., 129:1330-8 (2005).
Shinoka, et al., "Transplantation of a tissue-engineered pulmonary artery", New Engl. J. Med., 344(7):532-3 (2001).
Solan, Age effects on vascular smooth muscle: an engineered tissue approach., Cell Transplant., 14(7):481-8 (2005).
Stark, "The use of valved conduits in pediatric cardiac surgery", Peadiatr. Cardiol., 19:282-8 (1998).

(56) References Cited

OTHER PUBLICATIONS

Talacua, et al., "In Situ Tissue Engineering of Functional Small-Diameter Blood Vessels by Host Circulating Cells Only", Tissue Eng Pt A, 21(19-20):2583-94 (2015).
Tang, et al., "Geometric characterization of patient-specific total cavopulmonary connections and its relationship to hemodynamics", JACC Cardiovasc Imaging. 7:215-224 (2017).
Trojanowska, "Role of PDGF in fibrotic diseases and systemic clerosis", Rheumatology, 47:v2-v4 (2008).
Udelsman, et al., "Development of an operator-independent method for seeding tissue-engineered vascular grafts", Tissue Eng Part C Methods. 17(7):731-6 (2011).
Vacanti and Langer, "Tissue engineering: the design and fabrication of living replacement devices for surgical reconstruction and transplantation", Lancet, 354 Suppl 1:S132-4 (1999).
Van Rooijen and Sanders, "Liposome mediated depletion of macrophages: mechanism of action, preparation of liposomes and applications", J. Immunol. Methods, 174:83-93 (1994).
Viswanathan and Daley, "Lin28: A microRNA regulator with a macro role", Cell, 140(4):445-9 (2010).
Vorp, et al., "Effect of aneurysm on the tensile strength and biomechanical behavior of the ascending thoracic aorta", Ann Thorac Surg., 75:1210-4 (2003).
Watabe, et al., "TGF-beta receptor kinase inhibitor enhances growth and integrity of embryonic stem cell-derived endothelial cells", J. Cell Biol., 163:1303-11 (2003).
Watanabe, et al., "Tissue-engineered vascular autograft: inferior vena cava replacement in a dog model", Tissue Eng., 7(4):429-39 (2001).
Wolf, et al., "Antibodies against transforming growth factor-beta-1 suppress intimal hyperplasia in a rat model", Clinical Investigation, 93(3):1172-8 (1994).
Wynn and Barron, "Macrophages: master regulators of inflammation and fibrosis", Semin Liver Dis., 30(3):245-57 (2010).
Wynn, "Common and unique mechanisms regulate fibrosis in various fibroproliferative diseases", Clin. Invest. 117:524-9 (2007).
Wynn, "Fibrotic disease and the T(H)1/T(H)2 paradigm", Nat Rev Immunol. 4(8):583-94 (2004).
Wystrychowski, et al., "First human use of an allogeneic tissue-engineered vascular graft for hemodialysis access", J Vasc Surg 60(5):1353-7 (2014).
Zimmermann, et al., "Functional contribution of elevated circulating and hepatic non-classical CD14CD16 monocytes to inflammation and human liver fibrosis", PLOS One, 5(6):e11049 (2010).

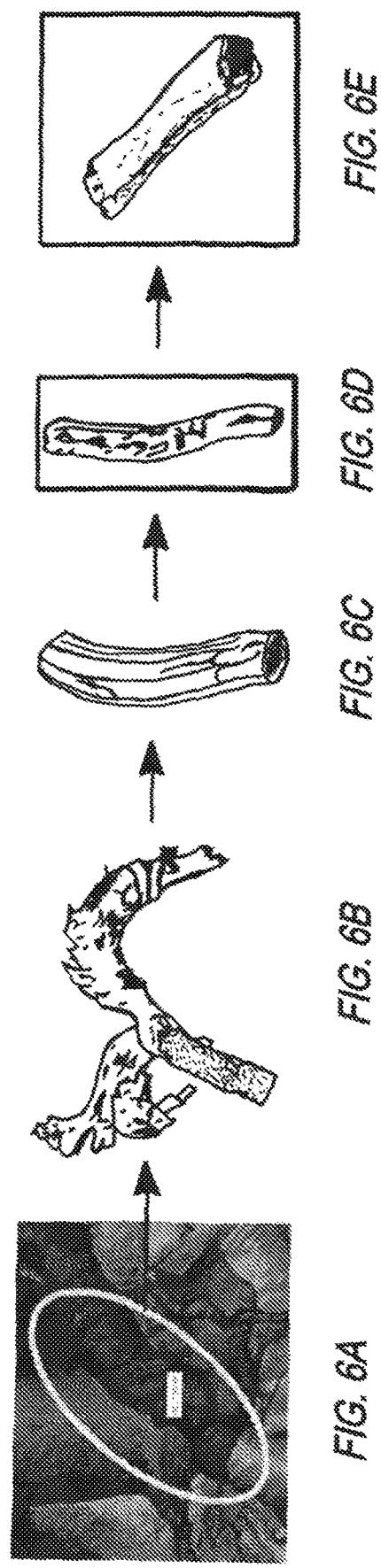

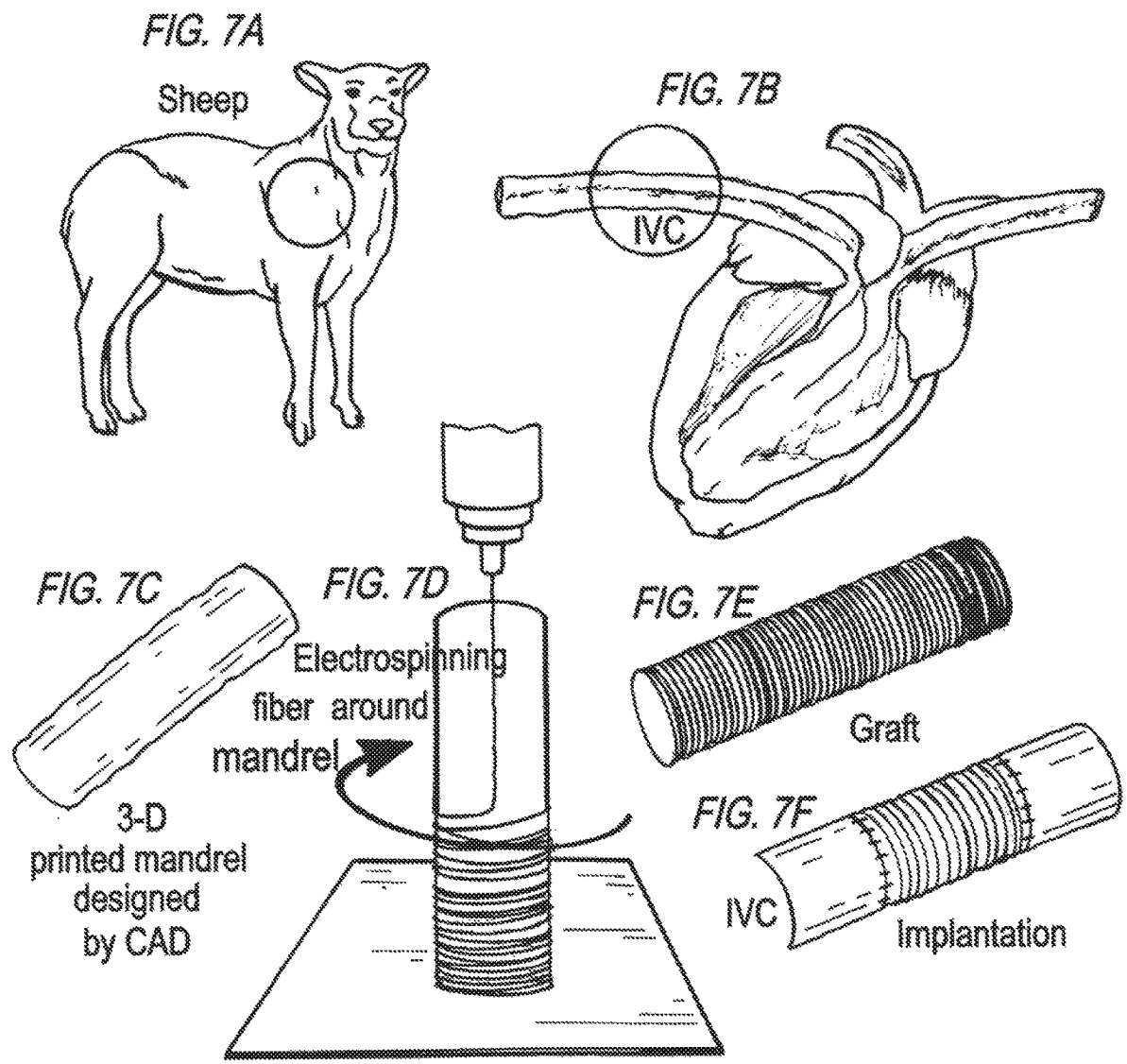

SYSTEMS AND METHODS FOR OPTIMIZED PATIENT SPECIFIC TISSUE ENGINEERING VASCULAR GRAFTS

CROSS-REFERENCE TO RELATED APPLICATIONS

This application claims benefit of and priority to U.S. Ser. No. 62/266,309 filed Dec. 11, 2015 and to U.S. Ser. No. 62/309,285 filed Mar. 16, 2016, both of which are incorporated by reference in their entirety.

STATEMENT REGARDING FEDERALLY SPONSORED RESEARCH OR DEVELOPMENT

This invention was made with Government Support under grant No. 1UH54HL119810-01 from the NIH Center for Accelerated Innovations: Technology Development Program to Narutoshi Hibino, and under NIH grant No. R01-HL098228 to Christopher Breuer. The Government has certain rights in the invention.

FIELD OF THE INVENTION

The present invention is generally in the field of tissue engineered grafts, particular those that are seeded with patient-specific cells and are designed to be absorbed and replaced by the patient's own tissues.

BACKGROUND OF THE INVENTION

Surgical treatment of many complex congenital cardiac anomalies involves implantation of synthetic conduits of materials such as GORE-TEX® and DACRON®. A common example of such an application is the total cavopulmonary connection (TCPC) for single ventricle anomalies. In some instances, the use of these synthetic grafts as conduits is complicated by progressive obstruction, susceptibility to infection, and risk of thromboembolic complications. In all instances, a significant limitation to cardiovascular reconstruction is lack of growth potential of synthetic implants. For TCPC, this may lead to sub-optimal management strategies including either postponement of completion of the Fontan circulation because of patient size, or oversizing of conduits, which results in sub-optimal flow characteristics such as expiratory phase back-flow and regions of flow stagnation.

Tissue-engineered vascular grafts (TEVGs) offer the potential to overcome these problems by providing a biodegradable scaffold in which autologous cells proliferate and mature into a physiologically functional blood vessel as scaffold polymers degrade (Shin'oka, et al. *N. Engl. J. Med.* 344(7), 532-533 (2001); Hibino, et al. *J Thorac Cardiovasc Surg.* 139(2), 431-436.e432 (2010 Roh J D, et al. Biomaterials. 29(10), 1454-1463 (2008); Hibino, et al. *FASEB J.* 25(8), 2731-2739 (2011); Hibino, et al. *FASEB J.* 25(12), 4253-4263 (2011); Kurobe, et al. *Tissue Eng Part C Methods* 21(1), 88-93 (2015)). However, current TEVGs do not directly address the diverse anatomic and physiologic requirements of individual patients. The first tissue engineered vascular graft (TEVG) with growth potential, designed specifically for use in congenital heart surgery was demonstrated previously (Brennan et al. *Ann Surg.* 248(3), 370-377 (2008); Isomatsu, et al. *J Thorac Cardiovasc Surg.* 126(6), 1958-1962 (2003); Shin'oka, et al. *N Engl. J. Med.* 344(7), 532-533 (2001)). Clinical trials in humans confirmed the growth capacity of the TEVG and demonstrated no graft related deaths or graft failures (Shin'oka, et al. *J Thorac Cardiovasc Surg.* 129(6), 1330-1338 (2005)). However, the results of this study also demonstrated that stenosis was the primary graft-related complication, effecting nearly 25% of graft recipients, with 16% of recipients developing critical stenosis (>75% decrease in luminal diameter) (Hibino, et al. *J Thorac Cardiovasc Surg.* 139(2), 431-436. e432 (2010)). Further, despite promising results using TEVGs for the treatment of patients with congenital heart diseases, the high incidence of graft stenosis in clinical applications hinders wide spread use of this technology (Fernandez, et al. *Current opinion in chemical engineering* 3, 83-90 (2014); Mcallister, et al. *Lancet* 373(9673), 1440-1446 (2009); Wystrychowski, et al. *J Vasc Surg* 60(5), 1353-1357 (2014)). Before routine clinical use of the TEVGs can be recommended, the assembly of the TEVG must be optimized to help inhibit the formation of TEVG stenosis and minimize the time required to make the graft and improve its overall utility (Patterson, et al. *Regenerative Medicine* 7(3), 409-419 (2012)). Imaging technologies, such as computed tomography (CT) and magnetic resonance imaging (MRI) provide surgeons detailed, three-dimensional (3D) views of complex cardiovascular anatomies before surgery. Translating this into a system that can be optimized in a practical, time and cost-efficient manner has proven difficult, however.

It is therefore an object of the present invention to provide methods and materials to making patient specific TEVGs, which can be seeded with a patient's own cells in two hours or less, and which will result in a patent graft not subject to stenosis in most cases.

SUMMARY OF THE INVENTION

Patient specific Tissue Engineering Vascular Grafts (TEVGs) using FDA approved biodegradable nanofiber materials such as poly(lactic acid-glycolic acid coated around 3D printed mandrel have been developed Seeding TEVGs with cells reduces the degree of macrophage infiltration, enhanced efficiency of cell attachment, reduced stenosis and enhances graft patency in a dose-dependent manner, whereas cell incubation time does not affect TEVG patency.

Patient-specific polymeric vascular grafts or conduits including an effective amount of viable cells to reduce or prevent post-operative stenosis of the graft relative to the graft without the cells or with less cells are provided. Typically, the graft has attached thereto an amount of viable cells between about $0.5 \times 10^3$ cells/mm$^2$ graft and $300 \times 10^3$ cells/mm$^2$ graft, inclusive, preferably between about $1.0 \times 10^3$ cells/mm$^2$ graft and $100 \times 10^3$ cells/mm$^2$ graft, inclusive. Preferred cells are obtained from the patient's bone marrow. In preferred embodiments, the vascular graft is seeded with viable cells are autologous cells. In a particular embodiment, the cells are human bone marrow mononuclear cells. The polymeric vascular graft or conduit can include one or more additional agents selected from the group consisting of anti-neointima agents, chemotherapeutic agents, steroidal and non-steroidal anti-inflammatories, conventional immunotherapeutic agents, immune-suppressants, cytokines, chemokines, and growth factors.

Patient-specific polymeric vascular grafts or conduits are created using computer aided design modeling of graft morphology; 3D-printing of a mandrel model of the graft; electrospinning of the graft based on the morphology of the mandrel; and seeding the graft with cells. Typically, the number of cells used to contact the graft or conduit is proportional to the surface area of the graft, wherein the number of cells is between about $1.0 \times 10^4$ cells/mm$^2$ graft and $1.0 \times 10^6$ cells/mm$^2$ graft, inclusive, preferably between $0.7 \times 10^5$ cells/mm$^2$ graft and $7.0 \times 10^5$ cells/mm$^2$ graft, inclusive. In some embodiments, the patient-specific polymeric vascular grafts or conduits are contacted with an amount of cells between $0.5 \times 10^6$ cells and $500 \times 10^6$ cells, inclusive, preferably between $1.0 \times 10^6$ cells and $100 \times 10^6$ cells. In preferred embodiments, the graft is contacted with the cells for less than 3 hours, preferably less than 2 hours. The contacting is typically carried out within a sterile, closed seeding chamber.

Methods for increasing the patency of a polymeric vascular graft or conduit, include the steps of administering an effective amount of viable cells onto the graft or conduit to reduce the infiltration of macrophages to the graft, to promote the recruitment of host cells to the graft or to reduce or prevent platelet activation are also provided.

Methods of reducing or reducing or preventing postoperative stenosis in a subject have been developed. The subject can be a subject at risk of or has restenosis or other vascular proliferation disorder. For example, in some embodiments, the subject has undergone, is undergoing, or will undergo vascular trauma, angioplasty, vascular surgery, or transplantation arteriopathy. The methods reduce or neointima formation, stenosis or restenosis, reduce or prevent thrombosis, or any combination thereof in a subject relative to an untreated control subject.

Customizable systems and compositions for seeding of cells into a patient-specific vascular graft or conduit are also provided. The systems are preferably closed, single-use and customizable systems for use with vacuum-assisted seeding of grafts with solutions containing one or more cell types. The systems can include a suction rod, a scaffold-specific mandrel, a scaffold fastener and a seeding chamber. In preferred embodiments, one or more of the suction rod, scaffold-specific mandrel, scaffold fastener and seeding chamber is produced by a method of 3D-printing. Systems including a patient-specific polymeric vascular graft or conduit are also provided. Methods of using customizable, single use systems for seeding of cells into a patient-specific vascular graft or conduit making patient-specific polymeric vascular grafts or conduits seeded with viable cells are also provided. Typically, the methods include the steps of computer aided design modeling of graft morphology; 3D-printing of a mandrel model of the graft; fabricating the graft based on the morphology of the mandrel; and seeding the graft with cells within the closed, disposable and customizable system for vacuum seeding.

BRIEF DESCRIPTION OF THE DRAWINGS

FIGS. 6A-6E provide a flow chart depicting the proposed process to manufacture patient-specific tissue engineered vascular grafts. FIG. 6A shows a segmenting 3D image of vasculature. FIG. 6B shows creation of a patient specific graft design from the preoperative CT image using computer aided design system. FIG. 6C is an image of the finalized image of a mandrel. FIG. 6D is an image of a 3D printed mandrel fabricated from stainless steel. FIG. 6E is a view of a patient-specific nanofiber graft.

FIGS. 7A-7F depict an exemplary schematic workflow illustrating the manufacturing and surgical implantation of a patient-specific nanofiber tissue engineered vascular graft in an animal (sheep) model system. The dimension and shape of the thoracic inferior vena cava (IVC) is measured from angiography prior to surgery in sheep model (FIG. 7A, B).

An electrospinning mandrel is modeled by computer aided design and subsequently 3D-printed (FIG. 7C). The nanofiber scaffold was electrospun onto the 3D printed mandrel (FIG. 7D). FIGS. 7E and 7F demonstrate implantation of a patient-specific cell-free nanofiber TEVG as an IVC interposition conduit in sheep model.

FIG. 9A is a graph showing Fold-Change (1.0-2.5) for each of Native IVC (●), Prox-TEVG (■), Mild TEVG (▲), and Dis-TEVG samples (▼), respectively. FIG. 9B is a graph showing Pressure Gradient (0-10 mmHg) for samples of 3 month and 6 month TEVG, respectively. FIG. 9C is a graph showing Elastin (0-10 µg/mg) for samples of Native IVC, and TEVG, respectively (**p=0.0045). FIG. 9D is a graph showing Collagen (1.4-2.4 µg/mg) for samples of Native IVC, and TEVG, respectively.

FIG. 11A is a graph showing Wall Thickness (mm) for each of Native IVC, and TEVG, respectively (**p=0.0091). FIG. 11B is a graph showing CD68+Macrophage/HPF over Wall thickness (mm).

DETAILED DESCRIPTION OF THE INVENTION

I. Definitions

Figure 1A:
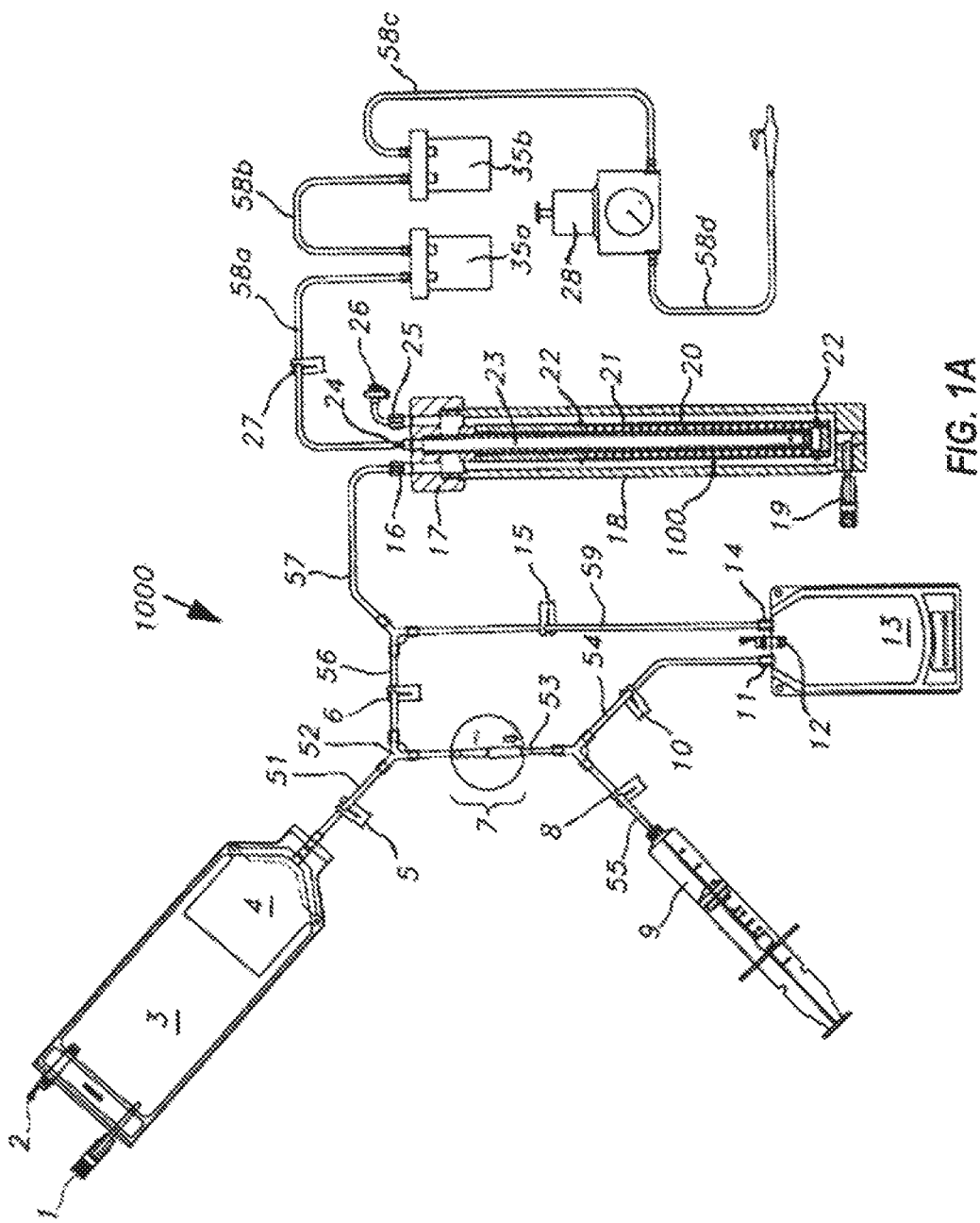
FIG. 1A is a diagram illustrating an exemplary closed system (1000) for seeding, culturing, storing, shipping and/or testing cells and/or grafts, e.g., tissue grafts.

The term "mandril" refers to a cylindrical device or tube, e.g., a metal bar, that serves as a core around which material, e.g., a matrix scaffold for seeding and growing cells, may be cast, molded, forged, bent, or otherwise shaped. In certain embodiments, the mandril described herein is open on at least one end. In additional embodiments, the mandril described herein may also contain holes or perforations along its axis (i.e., along its length).

The term "valve" refers to a device or part of a device by which the flow of liquid, gas, or loose material may be started, stopped, or regulated, e.g., by a movable part that opens, shuts or partially obstructs one or more ports (e.g., inlet or outlet) or passageways.

The term "biocompatible" refers to a material that the body generally accepts without a major immune response, which is capable of implantation in biological systems, for example, tissue implantation, without causing excessive fibrosis or rejection reactions.

The term "biodegradable" refers to the ability of a substance or material to break down when exposed to water, enzymes or in an in vivo environment.

As used herein, the term "porous" relates to having one or more openings, pores, perforations or holes that may be filled or perfused by a liquid and/or a gas, or that allows for the flow of a liquid and/or gas therethrough.

The term Tissue-Engineered Vascular Graft (TEVG) refers to a vascular graft or conduit devise that is designed for insertion into the body for use in the repair or augmentation of one or more vessels, such as arteries and veins.

The term "patient-specific graft" refers to a graft that is modelled according to the morphology of the intended site of insertion within the intended recipient. For example, computer-based imaging systems can be used to identify the precise orientation and shape of the site of insertion of the graft.

The term "Platelet Activation" is the step-wise physiological process that gives rise to adherence and aggregation of circulating platelets in response to tissue injury, such as damage or interruption of the endothelium. Platelet activation gives rise to expression and secretion of chemotactic agents such as platelet derived growth factor (PDGF) and transforming growth factor beta (TGFβ).

As used herein, "stenosis" refers to a reduction in lumen diameter of 75% or more.

II. Methods of Making Cell-Seeded TEVGs

Methods of making cell-seeded TEVGS, such as patient-specific TEVGS, are described. Typically, the cell-seeded TEVGs are manufactured according to the specific anatomical requirements of the intended site of application, and then seeded with cells. Methods for the custom design of patient-specific TEVG and the seeding of manufactured TEVGs with cells are described in more detail below.

A. Manufacture of Patient-Specific TEVGs

Methods of making polymeric vascular grafts or conduits for use as patient-specific tissue engineering vascular grafts (TEVGs) are provided. Typically, the methods include the steps of custom designing a mandrel model using image-assisted computational design methods, fabricating a mandrel model, for example, using 3D-printing, and fabrication of the TEVG from the mandrel model, for example, using electrospinning. An exemplary schematic workflow illustrating the manufacturing and surgical implantation of a nano-fiber graft in an animal is shown in FIGS. 6A-6E.

1. Custom Design of Patient-Specific Mandrel Models

Methods of making patient-specific TEVGs typically include one or more steps for the customized-design of the patient-specific graft.

TEVGs can be designed of any size and shape to optimally perform the function(s) required by the intended use. Typically, patient-specific TEVGs are substantially tubular in shape, with a round or substantially round cross section, and open-ended morphology. The tubular grafts have a lumen extending throughout the length of the graft. The grafts may be of any appropriate length and diameter that is suitable for the intended surgical use of the graft. Typically, the graft should be slightly longer than the length of artery or vein that is to be replaced or augmented. The thickness of the TEVG wall and the diameter of the TEVG itself can be uniform, or can be varied throughout the length of the graft, according to the intended use, and/or as defined by the computer-based design criteria. In some embodiments, the tubular grafts are porous conduits. The pores in the grafts allow for recruitment and integration of cells into the graft.

The custom design process can include the step of obtaining 3D images from the patient using imaging technologies such as ultrasound, computed tomography (CT), and magnetic resonance imaging (MRI) to provide detailed, three-dimensional (3D) views of complex cardiac and vascular anatomy of congenital heart disease before surgery. In some embodiments, images obtained from the patients are modified by a computer model for the purpose of printing a patient-specific mandrel model, and subsequent creation of a vascular graft, for example, by electro-spinning of a fiber to form a vascular graft around a custom mandrel. In preferred embodiments, the mandrel model is shaped to match a specific patient's anatomy. In some embodiments, the design criteria for modeling the mandrel includes the step of optimizing the shape and dimensions of the mandrel for fluid flow, for example, as computed based on flow dynamic simulations. Where mandrel models are designed based on preoperative angiography images, parameters such as the diameter and length of the vessel that is to receive the TEVG are measured, and matching graft models are designed, for example, using suitable computer software. Suitable software packages for the design of mandrel models based on pre-operative imaging data are commercially available. An exemplary software suite is the CAD software suite.

2. Fabrication of Mandrel Models

Mandrels for use in the formation of TEVGs can be fabricated using means known in the art. Exemplary methods for the fabrication of mandrels include 3D printing. In some embodiments, the final mandrel design is converted to a suitable computer-readable format for 3D fabrication. An exemplary computer-readable format is STL format. Suitable materials for 3D printing of mandrel models include polymers and metals and carbon, as well as combinations, alloys, and/or laminations thereof. In some embodiments, the mandrel is made of a liquefiable material, thereby allowing the release of the mandrel from the graft in an easy fashion. The use of liquefiable mandrels also allows for forming complex shapes of the graft. Typically, fabrication of custom-designed mandrel models is carried out in a small amount of time, such that patient-specific grafts can be produced within one week of surgery, or within one, two, three, four, five or six days of surgery.

3. Fabrication of Tissue-Engineered Vascular Graft (TEVG)

Methods of fabricating TEVGs based on a template structure, such as a custom-designed mandrel, are provided. TEVGs can be fabricated using any appropriate method, such as electrospinning, stamping, templating, molding, weaving and combinations melt processing, solvent processing, leaching, foaming, extrusion, injection molding, compression molding, blow molding, spray drying, extrusion coating, and spinning of fibers with subsequent processing into woven or non-woven constructs.

The dimensions of the TEVG are typically equivalent to the dimensions of the vessel to be replaced. In some embodiments, the TEVG have a length of from between about 1 mm and about 100 mm, inclusive, preferably between 3 mm and 10 mm. The inner diameter of the TEVG is typically equivalent to that of the vessel that is to be replaced. In some embodiments, the TEVG have an inner diameter of from between about 0.1 mm and 30 mm, inclusive, preferably between 0.5 mm and 1 mm. An exemplary TEVG is a polyglycolic acid sheet with a co-polymer sealant solution of poly-L-lactide and ε-caprolactone, having dimensions of 0.82 mm in inner diameter and 3 mm in length.

In some embodiments, TEVGs are fabricate to include pores in the graft Pores can be derived by any suitable method, including salt leaching, sublimation, solvent evaporation, spray drying, foaming, processing of the materials into fibers and subsequent processing into woven or non-woven devices. In a preferred embodiment, the fiber matrix of the scaffold includes pores of a suitable size to allow cells to adhere and grow and/or differentiate. Since the diameter of a cell is approximately 10 µm to 20 µm, pore sizes within this range are desired in certain embodiments. Preferably, the pores of the device are between 5 and 500 µm, more preferably between 5 and 250 µm, more preferably between 5 and 100 µm, in diameter. In certain embodiments, the polymeric scaffolds are generated or fabricated in order to more closely mimic the structure and composition of the natural extracellular matrix in order to promote growth and differentiation of the seeded cell and to facilitate transplantation and/or implantation of the scaffold or cells grown on the same.

In a preferred embodiment, TEVGs are fabricated by electrospinning of a stock solution containing one or more polymers. Typically, one or more polymers used to fabricate TEVGs are biodegradable polymers. Therefore, in some embodiments methods of fabricating TEVGs include the step of creating a pre-operative patient-specific electro spun fiber vascular graft. Preferably, the electro spun fiber grafts prepared according to the described methods promote cell adhesion and proliferation, and thereby prevent conduit stenosis (i.e., abnormal narrowing) and maintain vessel and graft patency.

B. Seeding of Patient-Specific TEVGs with Cells

It has been established that the cell-seeding dose on tissue engineered vascular graft (TEVG) is an effect-dependent variable for improving the performance and utility of the graft, regardless of cell incubation time. Typically, TEVGs are seeded with cells prior to implanting into a subject. Typically, the cells are autologous cells from the intended recipient, and the methods of seeding can include the step of harvesting the cells from the recipient. One or more cell types can be isolated from a mixture of cells using any techniques known in the art. Therefore, the methods can also include the step of isolating or purifying the cells prior to application (i.e., seeding).

Assembling a TEVG as used in the human clinical trial described in the Examples involves the steps of cell harvest and isolation, cell seeding onto the scaffold, and incubating the seeded graft for a period of time (Shin'oka, et al. *J Thorac Cardiovasc Surg.* 129(6), 1330-1338 (2005)).

In some embodiments, seeding of TEVG with cells is carried out using a kit or device. Preferably, the kit or device enables sterile and efficient seeding of TEVG with a controllable amount of cells.

1. Seeding Dose

Typically, the amount of cells seeded into the TEVG is directly proportional to post-operative graft patency. Therefore, in preferred embodiments, TEVGs are seeded with a sufficient amount of cells effective to enhance the patency, or reduce the rate of post-operative restenosis of the TEVG. Methods for manually seeding TEVGs with cells are known in the art (Udelsman, et al. *Tissue Eng Part C Methods.* 17(7), 731-736 (2011)).

The optimal number of cells seeded can vary according to the cell type, and the size and shape of the TEVG, as well as the intended use. TEVGs are typically contacted with an amount of cells between $1.0 \times 10^6$ cells and $500 \times 10^6$ cells, inclusive, preferably between $3.0 \times 10^6$ cells and $250 \times 10^6$ cells. An exemplary TEVG is a polyglycolic acid sheet with a co-polymer sealant solution of poly-L-lactide and ε-caprolactone, having dimensions of 0.82 mm in inner diameter and 3 mm in length. For a closed cylindrical TEVG, surface area (A) can be calculated according to the Formula I:

$$A = 2\pi rh + 2\pi r2$$

where h is the length of the TEVG, and r is the radius. For a tubular TEVG with nominal wall thickness, the available surface area of teach surface is 2πrh for the inner and outer surfaces, respectively.

For a TEVG is a having dimensions of 0.82 mm in inner diameter (0.41 mm in radius) and 3 mm in length, the available surface area is approximately 2(7.7283179) (i.e., approximately 15 mm$^2$). When seeded with $10 \times 10^6$ cells, the resulting seeding density is approximately a seeding density of $7.0\times10^5$ cells/mm². Therefore, in preferred embodiments, TEVG are seeded at a density of between about $1.0\times10^4$ cells/mm² and $1.0\times10^6$ cells/mm², inclusive, preferably between $0.7\times10^5$ cells/mm² and $7.0\times10^5$ cells/mm², inclusive.

In some embodiments, TEVGs are seeded with cells in solution having a concentration of between about $0.1\times10^4$ cells/ml and $10\times10^7$ cells/ml, inclusive. Typical volumes of cell solutions range between 1 ml and 100 ml, inclusive, preferably between 10 ml and 50 ml.

The number of attached cells/area increases in dose-dependent manner. Preferably, TEVGS are seeded with cells in an amount sufficient to yield a cell density of between $0.1\times10^3$ cells/mm² and $5.0\times10^3$ cells/mm², preferably between $1.0\times10^3$ cells/mm² and $2.0\times10^3$ cells/mm². This correlates to a seeding efficiency of about 10-20%. Therefore, for grafts seeded with autologous cells, increasing the amount of bone marrow harvested from patients increases the cell attachment in the graft in a dose dependent manner.

As demonstrated in the Examples, it has been established that cell seeding inhibits the formation of TEVG Critical Stenosis in a cell dose dependent manner, where "Critical Stenosis" represents a reduction in graft patency of at least 75%. Preferably, TEVG are seeded with an amount of cells effective to reduce the rate of stenosis by at least 50% relative to an un-seeded control. For example, in some embodiments TEVG are seeded with an amount of cells sufficient to reduce the amount of Critical Stenosis (i.e., a reduction in patency of at least 75%) at 2 weeks following implantation relative to an unseeded control graft by between 50% and 100%, e.g., 60%-90%, most preferably at least 64%.

When autologous bone marrow mononuclear cells (BM-MNCs) cells are prepared for seeding, the cells from 5 ml/kg of bone marrow are typically provide a sufficient seeding dose. From a clinical perspective, up to 20 ml/kg of bone marrow can be harvested from an individual without incurring significant adverse effects and is routinely used for harvesting bone marrow for bone marrow transplantations.

2. Seeding Methods

When the number of cells available for seeding is limiting, seeding of TEVG is preferably carried out using methods that maximize the efficiency of the contacting process, such that TEVG are contacted with as many cells as possible, in a manner that enhances the ability of seeded cells to adhere to the TEVG. Because the amount of cells that are contacted with TEVG is more significant in reducing post-operative stenosis and enhancing cell attachment than incubation time, the methods of seeding typically enhance the ability of the TEVG to contact the maximum numbers of cells in the shortest possible time, to enhance the efficacy of seeding.

Preferably, TEVG are contacted with cells in a suitable media (e.g., RPMI 1640 (Sigma)), and at a suitable temperature (e.g., at 37° C.) to optimize cell adhesion. In some embodiments the seeding is carried out in the presence of $CO_2$, for example, using a $CO_2$, incubator.

Methods and assays to measure seeding efficiency are described. Because the parameters that maximize cell seeding efficacy are dependent upon the cell type and graph morphology, one skilled in the art will recognize that it is possible to optimize the conditions of the seeding to maximize the number of a given cell types that can be seeded and attached to a given graft. An exemplary method to investigate the effect of cell seeding dose on the formation of TEVG stenosis includes seeded TEVGs with incrementally increasing numbers of cells, such as $0.1\times10^6$, $1\times10^6$, or $10\times10^6$ cells, respectively, alongside unseeded controls, and incubating the mixtures for a fixed time period. Post-operative stenosis can be assessed by methods known in the art. In an exemplary method, seeded TEVG are implanted into individuals and compared to assess for graft patency at a later time point, for example, two weeks following implantation.

It has been established that macrophage infiltration in TEVG occurs with a cell dose-dependent manner, such that increasing the number of cells seeded onto the TEVG reduces the amount of Macrophage infiltration relative to an unseeded control, or TEVGs seeded with a minimal number of cells.

An exemplary method to investigate the effect of cell seeding dose on Macrophage infiltration of TEVG includes seeded equivalent TEVGs with incrementally increasing numbers of cells, such as $0.1\times10^6$, $1\times10^6$, or $10\times10^6$ cells for a fixed time period, and inserting the seeded TEVGs into a individual. To determine whether cell dose affects macrophage infiltration into the TEVG, the number of infiltrating macrophages is evaluated at a time following implantation, such as two weeks following implantation. An exemplary method for evaluating macrophage infiltration is quantitative histological morphometric analysis.

Therefore, the dose of cells used to seed TEVG is preferably sufficient to reduce macrophage infiltration into the TEVG as compared with an unseeded or minimally seeded control.

In an exemplary embodiment, the effect of cell seeding dose on cell attachment and seeding efficiency of a TEVG is determined by contacting cells with the TEVG and incubating the mixture with incrementally increasing numbers of the cells, such as $0.1\times10^6$, $1.0\times10^6$, and $10.0\times10^6$ cells, for a fixed time period. The efficacy of cell adhesion as a function of cell dose can be determined using any suitable assay for cell counting. An exemplary assay is an in-vitro DNA assay.

a. Cell Incubation Time

To insure the best clinical outcome using TEVG technology, it is important to optimize the time for TEVG assembly, to minimize the time for the surgical procedure, decrease the potential for contamination, and thereby decrease the risk associated with using this technology.

Figure 2A:
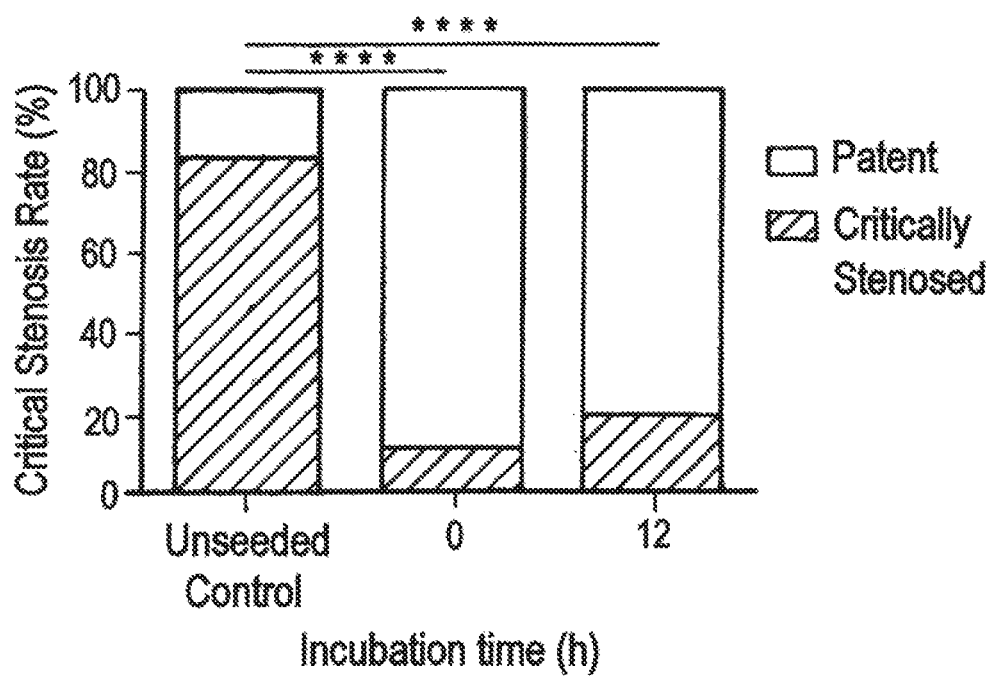
FIGS. 2A and 2B are histograms showing Critical Stenosis Rate (%), as determined by the percentage of Patent (□) vs. Critically Stenosed (■) grafts over Incubation time (hours) for each of unseeded (control) and seeded samples incubated for 0 hours and 12 hours, respectively ($p<0.0001$) (FIG. 2A); and over Cell Seeding Dose ($\times 10^6$) for each of unseeded (control) sample, and samples seeded with 0.1, 1.0 and $10.0 \times 10^6$ cells, respectively ($p<0.0001$) (FIG. 2B).

Because the duration of cell incubation does not affect TEVG patency (as discussed in the Examples and FIGS. 2A and 2B), in certain embodiments the time required to assemble seeded TEVGs can be minimized by reducing the amount of time incubation time that seeded cells are contacted with the TEVG.

The time required to assemble the TEVG was previously reduced using a closed disposable system that reduced the time for cell isolation and seeding without affecting TEVG patency (Kurobe, et al. *Tissue Eng Part C Methods* 21(1), 88-93 (2015); Kurobe, et al. *Tissue Eng Part C Methods*, (2014)). In the initial human clinical trial discussed in the Examples, a two hour incubation time was selected arbitrarily, however the optimal incubation time is important to enhance TEVG assembly without affecting patency of the TEVG, as well as for improving safety of the patients.

The studies described in the Examples refine the assembly of the TEVG with a focus on cell dosing and optimal incubation time. In an exemplary embodiment, the effect of duration of incubation time on cell attachment and seeding efficiency of a TEVG is determined by contacting cells with the TEVG and incubating the mixture for incrementally increasing time periods, such as 0, 0.5, 2, and 12 hours. The efficacy of cell adhesion as a function of incubation time can be determined using any suitable assay for cell counting. An exemplary assay is an in-vitro DNA assay.

In some embodiments, the methods include contacting the TEVG for a period of time that is less than 5 hours, for example, 4 hours, 3 hours, 2 hours or less than 2 hours. In preferred embodiments, the TEVG is contacted with cells for less than two hours, for example, 60 minutes or less than 60 minutes, for example up to 50 mins, up to 40 mins, up to 30 mins, or less than 30 mins. In some embodiments, the TEVG is contacted with cells in a flowing solution. The flow rate can be adjusted to optimize cell permeation throughout the TEVG. For example, in some embodiments, the incubation time is equivalent to the amount of time required to passage the desired quantity of cells through the TEVG.

III. Materials for Making TEVGs

Polymeric vascular grafts or conduits including polymers and cells are described. The polymeric vascular grafts or conduits can optionally include additional active agents.

A. Polymers

TEGV scaffolds can be synthesized from one or more polymers.

In some embodiments, the polymers are biodegradable. In other embodiments, the polymers are non-biodegradable. In some embodiments TEVG are formed from a mixture of more than a single polymer. When biodegradable polymers are used, mixtures of biodegradable and non-biodegradable polymers can be used, for example, to provide long-lasting TEVG implants, as desired.

In certain embodiments, TEVGs are a three-dimensional matrix formed of polymeric (homopolymer and/or copolymer) fibers that are assembled in a woven or non-woven mesh, in random or aligned configurations. Preferably, the nanofiber materials are FDA approved biodegradable nanofiber materials.

The fibers comprising the scaffold matrix can be of any desired size, but generally are between about 1.5 mm and 1 nm. In certain embodiments, the fibers are nanoscale (i.e., from about 1 nm to about 1000 nm) and/or microscale (from about 1 μm to about 1000 μm).

Polymers useful for creating a scaffold for use in formation of TEVGs may be inorganic (e.g., siloxane, sulfur chains, black phosphorus, boron-nitrogen, silicones) or organic (meaning containing carbon). Organic polymers may be natural (e.g., polysaccharides, such as starch, cellulose, pectin, seaweed gums, vegetable gums; polypeptides, such as casein, albumin, globulin, keratin, collagen, insulin, DNA; and hydrocarbons), synthetic (such as thermoplastics (unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)). In addition, scaffolds useful in the present invention may include hydrogels formed from water soluble or water insoluble cellulose compounds. As would be readily understood by the skilled artisan, the particular type and composition of scaffold will vary depending upon the desired application. However, it is generally preferred that the polymeric material comprising the scaffold be biocompatible (i.e., will not elicit an unwanted immune reaction). In certain embodiments, the scaffold is biodegradable. Exemplary degradable polymers include poly(lactic acid-glycolic acid), a poly(lactic acid), a poly(glycolic acid), a poly(orthoester), a poly(phosphazene), poly(or polycaprolactone, a polyamide, a polysaccharide, and a collagen. In a preferred embodiment, the polymer is poly(lactic acid-glycolic acid). In one embodiment, patient-specific TEVGs are formed from a biodegradable tubular scaffold fabricated from a polyglycolic acid-fiber tube. The tube can be coated with a copolymer such as a 50:50 ratio of poly lactic acid (PLA) and poly-caprolactone.

In one embodiment, the grafts are formed from a felt or sheet like material of the polymer that can be formed into a tubular conduit. For example the device could be fabricated as a nonwoven, woven or knitted structure from extruded polymeric fibers. Typically, the polymeric sheet is formed using any textile construction, including, but not limited to, weaves, knits, braids or filament windings. Any suitable method, such as electrospinning, can be used to fabricate the nonwoven or woven polymeric textile.

The polymers and fabrication methods selected to fabricate the polymeric vascular grafts are suitable to produce grafts with biomechanical properties suitable for use as vascular conduits. Biomechanical properties that are important for vascular graft function include initial burst pressure, suture retention strength and elasticity. In one embodiment, the initial burst pressure of the polymeric vascular graft is between about 1,500 mmHg and about 50,000 mmHg, preferably between about 2,000 mmHg and about 10,000 mmHg. In another embodiment, the polymeric vascular grafts possess suture retention strengths between about 1 N and about 5 N, preferably between about 2 N and about 4 N. In another embodiment, the intrinsic elasticity of the vascular grafts is between about 10 MPa and about 50 MPa, preferably between about 15 MPa and about 40 MPa. In another embodiment, the initial tensile strength of the vascular grafts is between about 1 MPa and about 10 MPa, preferably between about 3 MPa and about 6 MPa.

B. Cells

In certain embodiments, patient-specific TEVGs scaffolds include one or more types of cells. In some embodiments, one or more types of cells are included within the lumen of the TEVG, within porous spaces throughout the walls of the TEVG, on the exterior and surface of the TEVG, or combinations. Typically, cells are attached to the surface of the TEVG, either directly, or through one or more accessory substances. Exemplary accessory substances include polymers, polysaccharides, proteins, small molecules, lipids and cells. In some embodiments, the cells are autologous cells, derived from one or more tissues of the intended recipient of the cell-seeded TEVG. In other embodiments, the cells are exogenous to the intended recipient of the graft. The cells can be un-differentiated cells, such as pluripotent stem cells, or differentiated cells. In preferred embodiments, the cells are viable human cells. Exemplary cell types for inclusion in TEVGs include immune cells, such as T cells, B cells and antigen-presenting cells, fibroblasts, myofibroblasts fibroblast cells, smooth muscle cells, bone marrow progenitor cells, red blood cells, embryonic stem cells, and combinations. In a particular embodiment, autologous bone marrow mononuclear cells (BM-MNCs) are included within the TEVG.

Cells for use with the described patient-specific TEVGs can be obtained from multiple sources. Methods for isolating and optionally manipulating one or more cell types from mixtures of cells are known in the art. In an exemplary embodiment, bone marrow is collected from the one or more long bones (e.g., femurs and/or tibias) of a subject (e.g., the intended recipient of the TEVG) and mononuclear cells are isolated using the density centrifugation method (Lee, et al. *J Vis Exp.* (88), (2014); Udelsman, et al. *Tissue Eng Part C Methods.* 17(7), 731-736 (2011)).

C. Additional Active Agents

It has been established that TEVG seeded with bone marrow-derived mononuclear cells reduce and prevent the incidence of post-operative stenosis via a paracrine effect. Advantages of cell seeding include the release signals in response to the body's feedback mechanism, unlike the drug-eluting scaffolds which release the drug regardless of feedback. Therefore, in some embodiments, cell-seeded TEVG are used in combination with one or more non-cell based synthetic or non-synthetic compounds that replicate the paracrine effect of seeded cells.

Patient-specific TEVG can include additional active agents, for example, that enhance the adhesion of cells to the vascular graft, or reduce the incidence of post-operative stenosis of the graft following insertion. Active gents include, but are not limited to, anti-neointima agents, chemotherapeutic agents, steroidal and non-steroidal anti-inflammatories, conventional immunotherapeutic agents, immune-suppressants, cytokines, chemokines, and growth factors.

Use of growth factors to stimulate bone marrow growth represents an additional strategy for increasing the yield of BM-MNC. Therefore, in some embodiments, the TEVGS include growth factors. Exemplary growth factors for incorporating into TEVGS include growth factors released in the physiological response to tissue injury, which stimulate the deposition of extracellular matrix, such as Platelet-Derived Growth Factor (PDGF), a potent chemotactic agent, and Transforming Growth Factor beta (TGF-β).

IV. Methods and Materials for Seeding TEVGs with Cells

A. Systems for Seeding TEVGs

Systems and methods thereof for seeding TEVGs with cells are known in the art. An exemplary system is described in U.S. Pat. No. 9,090,863 (FIG. 1A). The device illustrated in FIG. 1A is a closed system (1000) for seeding, culturing, storing, shipping and/or testing cells and/or grafts, e.g., tissue grafts. The operation, structure, and results of prior seeding systems are discussed and illustrated further in U.S. Pat. No. 9,090,863 and in *Tissue Engineering Part C: Methods*. (1):88-93 (2014).

Typically, systems for seeding of cells into tissue engineered vascular grafts include means for creating a vacuum that is connected to a patient for extracting biological material from the patient, into a chamber or scaffold. The scaffold acts as an incubator, allowing at least a portion of the biological material to contact and interact with the scaffold. The scaffold is in fluid communication with a filter/switch combination that allows selectable fluids to transfer from the biological material, back into the patient. An exemplary biological materials that are transferred back into the patient include serum, red bloods, platelets, white blood cells and combinations. Extracting selected biological materials from the fluid that contacts the scaffold reduces the time required for seeding the scaffold with a desired cell types, and increases healing rates in the patient.

1. Components of Seeding Systems

The component parts of an exemplary system, described in U.S. Pat. No. 9,090,863, are illustrated in FIG. 1A. In certain embodiments, the system includes a vessel for containing a cellular isolate, e.g., a cellular isolate fluid, such as a container (3). Exemplary containers include a media bag or any flexible or rigid container capable of being sterilized and/or that is hermetically sealed (e.g., Gibco-BFL 1 L media bag). In certain embodiments, the cellular isolate fluid container (3) is formed from of a biocompatible, rigid material capable of being sterilized, such as Teflon, polycarbonate, PVC, or stainless steel. The container (3) can have any suitable volume for containing the cellular isolate fluid. In a preferred embodiment, the container (3) has at least one port adapted for the sterile filling and/or dispensing of a fluid, for example, a bone marrow aspirate. For example, a bone marrow aspirate (e.g., 5 cc/kg body weight) is aseptically collected and passed, e.g., injected, into container (3) via port (1) or port (2).

Typically, the container (3) has at least one inlet and one outlet. In some embodiments, the container (3) includes a port having one or more valves to allow for the one-way flow of a fluid or gas. For example, using the embodiment shown in FIG. 1A for reference, port 1 can include and/or take the form of a swabbable valve, such as a needleless access port. The valve can be connected to container (3), and/or can be associated with a fluid line communicating with the container (3), using any suitable coupling or fastening means which is known to those in the art, e.g., a clamp, screw or luer connector, pressure fitting, friction fitting, coupling or the like. In accordance with the embodiment of the system (1000) illustrated in FIG. 1A, valve (5) is associated with a conduit, e.g., a fluid line (51), communicating with the container (3). Optionally, the container (3) includes a pre-filter element (4), e.g., including, for example, a screen or woven element having openings or a pore structure in the range of, for example, about 40 to about 150 microns. Such pre-filter element could be used to remove undesirable material such as, e.g., bone chips, clots, and/or fat deposits, as the fluid passes from the container.

In certain embodiments, the means for containing a cellular isolate fluid includes a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

Examples of fluid which may be used in the system include, but are not limited to, sterilizing fluid, contrast media fluid, biological fluid, fluid containing cells, blood, serum, bone marrow aspirate, or fluid containing a culture medium. It is to be understood that during testing, seeding, and culturing in a preferred embodiment, the fluid may be advantageously kept at human body temperature, and may be composed of a fluid which approximates the viscosity of human blood. One illustrative example of a solution which approximates the viscosity of blood is saline with glycerol.

The fluid contained in container (3) is passed from the container through fluid line (51) of FIG. 1A. In a preferred embodiment, the fluid is directed away from container (3) by a vacuum. In other embodiments, the system incorporates the use of a fluid pump. Fluid pumps are available from multiple commercial sources (e.g., Masterflex L/S Digital Drive peristaltic pump manufactured by Cole-Palmer).

Fluid line (51), as well as all other fluid lines in the system (e.g., lines 52, 53, 54, 55, 56, 57, 58a-58d, and 59), may be made of any type of medical grade, sterilizable, durable tubing suitable for transporting the fluid or gas in use. For example, the fluid line can be flexible or rigid plastic.

The system also includes a flow channel (7) comprising at least one inlet, at least one outlet and at least one filter including at least one filter medium (e.g., disposed in a filter housing) between. In a preferred embodiment, the filter is disposed at an angle that is approximately perpendicular to the direction of flow through the flow channel (7), although in some embodiments, the filter can be disposed at an angle approximately parallel to the direction of flow, e.g., involving tangential flow filtration. In preferred embodiments the filter is adapted to allow flow through in at least two directions, for example, where the first and second directions are approximately opposite, e.g., wherein a fluid can be passed in a first direction from the upstream surface of the filter through the downstream surface, and a fluid can be passed in a second direction from the downstream surface of the filter though the upstream surface. In an example of this embodiment, a cellular isolate fluid is passed in a first direction through a filter having a suitable pore size (or mesh size), wherein the filter medium is at an angle that is approximately perpendicular to the direction of flow such that the filter retains cells and/or biological material that is too large to pass through the filter. A second fluid is subsequently passed in a second direction through the filter which can wash the retained cells and/or biological material off of the filter medium. Filters that can be employed for use in the flow channel are well known in the art and include, for example, Pall Corporation. In still additional embodiments, the filter (e.g., at least one filter medium) has a porosity suitable to retain cells, e.g., bone marrow-derived mononuclear cells. In certain embodiments, the filter includes a matrix that is designed to reversibly bind and retain the cells of interest based upon, for example, ligand-receptor interactions. In other embodiments, multiple filters can be assembled in series or in parallel for use in the system as described herein. It is contemplated that the system and method can have any number of desired flowpaths and shutoffs. The liquid or gas can be fed through the system by positive pressure or negative pressure, such as via a syringe, pump, or vacuum source, all of which are expressly encompassed and contemplated by the present invention.

In certain embodiments, the system includes a means for containing a collection fluid. In certain embodiments the means is a container (13), such as a media bag or any flexible or rigid container capable of being sterilized and/or that is hermetically sealed (e.g., Gibco-BFL 1 L media bag). In certain embodiments, collection container (13) is formed from any biocompatible, rigid material capable of being sterilized such as Teflon, polycarbonate, acrylic, PVC, or stainless steel. Container (13) can have any suitable volume for containing the collection fluid.

In a preferred embodiment, the container (13) has at least one port adapted for the sterile filling and/or dispensing of a fluid, for example, a bone marrow aspirate filtrate or flow through. For example, a bone marrow aspirate (e.g., 5 cc/kg body weight) is aseptically collected and passed, e.g., injected, into container (3) and subsequently passed (e.g., through optional pre-filter (4) and via fluid flow lines (51) and (52) through flow channel (7) including a filter. The filter retains cells and/or the biological material of interest, allowing the filtrate to flow through fluid lines (53) and (54) and inlet port (11) into container (13). In another preferred embodiment, the container (13) has at least one flow port, e.g., a bi-directional flow port; typically, however, the container (13) has at least two ports. In certain embodiments, container (13) includes an inlet port and/or an outlet port. In the embodiment illustrated in FIG. 1A, container (13) includes an inlet port (11) and an outlet port (14). In still another embodiment, the container (13) includes a port having one or more valves to allow for the one-way flow of a fluid or gas. The valve can be connected to container (13) and/or associated with a fluid line communicating with container (13) using any suitable coupling or fastening means which is known to those in the art, e.g., a clamp, screw or luer connector, pressure fitting, friction fitting, or the like. In accordance with the embodiment illustrated in FIG. 1A, the system (1000) includes a valve (10) associated with the fluid line (54).

In certain embodiments, the means for containing the collection fluid includes a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

In certain embodiments (e.g., after elution fluid is passed through the flow channel (7) and cells are passed into seeding container (18) as noted in more detail below), the collection fluid or filtrate contained in container (13) is passed through fluid lines (59) and (57) into seeding container (18) (in FIG. 1A).

In a preferred embodiment, the fluid is directed away from container (13) by a vacuum. In other embodiments, a fluid pump is used (e.g., Masterflex L/S Digital Drive peristaltic pump manufactured by Cole-Palmer, although one skilled in the art could select from a variety of commercially available pumps).

In certain embodiments, the system includes a means for containing an elution fluid. In certain embodiments, the means is a container (9), such as a media bag, syringe, or any flexible or rigid container capable of being sterilized and/or that is hermetically sealed (e.g., a Gibco-BFL 1 L media bag). In certain embodiments, elution fluid container (9) is formed of any biocompatible, rigid material capable of being sterilized such as Teflon, polycarbonate, acrylic, PVC, or stainless steel. Container (9) can have any suitable volume for containing the elution fluid.

In a preferred embodiment, the container (9) has at least one port adapted for the sterile filling and/or dispensing of a fluid, for example, an elution or washing fluid. In certain embodiments, the elution fluid can be a cell culture media, saline, e.g., phosphate buffered saline, saline including dextran, or any other suitable fluid known by those of skill in the art for harvesting or culturing cells, e.g., lactated ringers solution, normal saline, Delbecco's modified Eagles medium, a fluid as disclosed in International Publications WO 98/045413 and WO 05/094914, etc. In another preferred embodiment, the container (9) has at least one flow port, e.g., a bi-directional flow port. In certain embodiments, container (9) includes an inlet and/or an outlet. In still another embodiment, the container (9) includes a port having one or more valves to allow for the one-way flow of a fluid or gas, and/or one or more valves is associated with a fluid line communicating with the container (9). In accordance with the embodiment illustrated in FIG. 1A, the system (1000) includes a valve (8) associated with the fluid line (55). The valve can be connected to container (9) and/or associated with the fluid line using any suitable coupling or fastening means which is known to those in the art, e.g., a clamp, screw or Luer connector, pressure fitting, friction fitting, or the like. The elution or wash fluid is passed through valve (8) and fluid line (53), flow channel (7), fluid lines (52), (56), and (57), into seeding container (18) in FIG. 1A.

In certain embodiments, the means for containing the elution or wash fluid includes a body defining a sterile and/or hermetically sealed container capable of retaining a fluid or gas, wherein the body also defines one or more ports adapted for the filling and/or dispensing of a fluid. In certain embodiments, the body defines one or more ports, wherein at least one port has a valve, e.g., a one-way valve. In still another embodiment, the body defines an outlet port which includes a valve.

In one embodiment, container (9) is a syringe filled with a sterile elution or wash fluid. The elution or wash fluid is passed through flow channel 7 and into seeding container (18) through valve (8), fluid lines 53, 52, 56 and 57 in FIG. 1A. In this embodiment, the fluid is directed away from container 9 due to pressure exerted on the fluid by depressing the syringe plunger, for example, manually or via a mechanical and/or electrical device. Alternatively, for example, the container (9) can be a flexible container that can be compressed. However, as one of skill in the art would readily appreciate, a fluid pump could also be used (e.g., Mastedlex L/S Digital Drive peristaltic pump manufactured by Cole-Palmer, although one skilled in the art could select from a variety of commercially available pumps).

In certain embodiments, the system includes a means for containing a cell seeding assembly. In certain embodiments, the means is a seeding container (18), such as a media bag or any flexible or rigid container capable of being sterilized and/or that is hermetically sealed. For example, a Gibco-BFL 1 L media bag could be used. In certain embodiments, container 18 may be composed of any biocompatible, rigid material capable of being sterilized such as Teflon, polycarbonate, acrylic, PVC, or stainless steel. Seeding container (18) can have any suitable volume.

In certain embodiments, seeding container (18) may include two or more sections which are secured and made leak proof through any standard means, such as inner and outer threads or the use of bonding agents. For example, in accordance with the embodiment illustrated in FIG. 1A, the seeding container (18) includes a rigid material comprising a main body section including threads, and a threaded cap (17). Alternatively, the seeding container includes a flexible material such as a bag. In order to view the scaffold or graft, e.g., vascular graft, within container, a viewing port may be placed at any point or location on the container, or alternatively, the container may be made of an optically clear material such as polycarbonate or PVC.

In a preferred embodiment, the seeding container 18 has at least one port adapted for the sterile filling and/or dispensing of a fluid, for example, an elution or wash fluid and/or collection or filtrate fluid as described herein. In certain embodiments, container (18) includes an inlet and/or an outlet. In still another embodiment, the container (18) includes at least an inlet and an outlet port (in the embodiments illustrated in FIG. 1A, seeding container (18) includes an inlet port (16), an outlet port (24), a sampling port (19) (e.g., for aseptic acquisition of fluid samples from the seeding container to determine, for example, microbial contamination and/or stem cell enumeration), and a vent port (26), wherein the cap 17 (FIG. 1A) includes the ports). Using the embodiments shown in FIG. 1A for reference, port 19 can include a swabbable valve, such as a needleless access port. In a particularly preferred embodiment, the outlet port is adapted with a cell seeding assembly. In certain embodiments, the container (18) includes an inlet port having one or more valves to allow for the one-way flow of a fluid or gas. Alternatively, or additionally, one or more valves can be associated with one or more fluid lines communicating with the seeding container. The valve can be connected to container 18 and/or associated with a fluid line communicating with seeding container 18 using any suitable coupling or fastening means which is known to those in the art, e.g., a clamp, screw or luer connector, pressure fitting, friction fitting, or the like.

In a preferred embodiment, seeding container 18 includes an inlet port 16 and outlet port 24, which allows for the perfusion and/or circulation of fluid into and through the container. Inlet port 16 and outlet port 24 are also used to attach container 18 to fluid lines 57 and 58a, respectively. Fluid line 58a connects seeding container 18 to one or more residual seeded cell fluid containers 35a and 35b, while maintaining a closed system. It is to be understood that although only one seeding container 18 is shown in FIG. 1A, a fluid line, e.g., fluid line 57 or 58a, may be branched so as to connect more than one seeding container in parallel to the system.

Optionally, the seeding container 18 can further includes at least one vent, e.g., comprising at least one hydrophobic microporous membrane (preferably, disposed in a housing) as disclosed in, for example, International Publication WO 91/017809. For example, in the embodiments illustrated in FIG. 1A, a vent 26, preferably, providing a bacterial blocking pore rating, can be placed in communication with at least one seeding container port 25. Without being bound to any particular theory or mechanism, the vent may allow for gas exchange, e.g., while the seeded scaffold is bathed.

In certain embodiments, the means for containing the seeding assembly includes a body defining a sterile and/or hermetically sealed container capable of retaining a fluid or gas, wherein the body also defines one or more ports adapted for the filling and/or dispensing of a fluid, and a seeding assembly. In certain embodiments, the body defines one or more ports, wherein at least one port has a valve, e.g., a one-way valve. In still another embodiment, the body defines an outlet port.

In certain embodiments, the means for containing residual seeded cell fluid is at least one residual seeded cell fluid container 35a, 35b, such as a media bag or any flexible or rigid container capable of being sterilized and/or that is hermetically sealed. For example, a Gibco-BFL 1 L media bag could be used. In certain embodiments, containers 35a, 35b may be composed of any biocompatible, rigid material capable of being sterilized, such as Teflon, polycarbonate, PVC, or stainless steel.

In a preferred embodiment, fluid is drawn out of container 18 into a residual seeded cell fluid container 35a via port 25 and fluid line 58a through the use of vacuum assembly comprising a vacuum source, e.g., a pump, and a regulator 28, wherein the negative pressure from the pump is conveyed through fluid lines connected to residual seeded cell fluid container 35a, 35b and seeding container 18.

In certain embodiments, seeding container (18) houses a seeding assembly (100) comprising a porous tube (20) and a scaffold (21), e.g., cell or tissue scaffold or graft, such as a vascular graft scaffolding. The porous tube (20) may include any suitable rigid material, such as Teflon, PVC, polycarbonate, plastic, metal, e.g., stainless steel, which may be made fluid permeable. One illustrative example of a suitable porous tubing is the porous plastic tubing manufactured by Porex Technologies. Alternatively, porous tube 20 may include any suitable elastomeric material, such as PET or angioplasty balloons, that is capable of expanding and contracting, and that may be made fluid permeable. Seeding container 18 and tube 20 may both be made any length or diameter so as to hold vascular graft scaffolding 21 of any length or diameter. This is advantageous, as the system may be used to sterilize, seed, culture, store, ship, and test vascular grafts of any size. One or more retaining elements such as clips (60), o-rings, or grommets may also be placed on tube, e.g., at both ends of scaffolding (21), to hold the scaffolding in place on the tube during seeding, culturing, storing, shipping, or treatment.

In certain embodiments, the porous tube (20) includes a mandrel. An exemplary mandril is illustrated in FIG. 12C/12D. With reference to FIG. 12C/12D: the open end of the mandril manifold is inserted over the suction rod (23) having an aperture near the closed end of the suction rod. The mandril is then affixed, e.g., with appropriate sized coupling rings, which are then inserted over the perforated mandril, and, illustratively, the mandril is frictionally held in the seeding container (18) via one or more o-rings (22) (shown in FIG. 1A). In some embodiments, the o-rings (22) are clips, such as hinged clips (60) (shown in FIGS. 1F, 1G). This assembly allows for the movement of fluid through the mandril manifold into the aperture and out the opening. As described herein, fluid is directed out of the seeding container (18) via suction rod (23) through the mandril via a vacuum means (for example a pump) communicating with residual seeded cell fluid containers 35a, 35b, and to the mandril through fluid lines 58a-58d.

In a preferred embodiment, the mandril includes a plurality of holes or perforations. However, it should be understood that the perforations may be of any desired size, shape, and/or configuration, which can be varied in any number of ways that would be obvious to the skilled artisan in view of the present description, and are encompassed and contemplated by the present invention. It is also contemplated that the porous tube (20) can be of any desired length and/or diameter. For example, the diameter may be varied to account for different graft sizes and/or applications, which are expressly encompassed and contemplated by the present invention.

In certain embodiments, the seeding container (18) houses a seeding assembly (100) comprising a porous tube (18) and a scaffold (21).

In any of the embodiments described herein, the scaffold can be apposed to the porous tube, e.g., a mandrel as described herein, in the seeding assembly. For example, it is contemplated that the scaffold may be in contact with only a portion of the porous tube. Alternatively, it is contemplated that the scaffold may substantially surround some or all of the porous tube. In general, it is preferred that the scaffold be in juxtaposition or adjacent to the perforated portion of the porous tube such that fluid flows through as much of the scaffold as possible to facilitate seeding of as many cells as possible.

In accordance with embodiments of the invention, a plurality of seeding containers, e.g., comprising seeding assemblies comprising porous tubes (preferably, mandrils and scaffolds) can be pre-assembled, e.g., for different size grafts and/or different applications, and assembled as part of the system when desired. Typically, for example, the seeding containers are pre-assembled and sterilized, and can be sterilely connected to the rest of the system, e.g., by sterile docking. Thus, the optimal system can be quickly set up when needed.

In another preferred embodiment, the flow channel is positioned between the cellular isolate container, collection fluid container, elution or wash fluid container, and the seeding container. This configuration is exemplified by FIG. 1A. In still another embodiment, the flow channel is selectively in fluid communication with each of the same. In an embodiment, a housing includes the flow channel, including an inlet, outlet, and filter comprising at least one filter medium, e.g., a porous leukocyte depletion medium (for example, in a preferred embodiment, the flow channel includes filter device comprising a housing having an inlet and an outlet and defining a fluid flow path between the inlet and an outlet, and a filter comprising at least one porous filter medium disposed in the housing across the fluid flow path). In another embodiment the housing includes the flow channel, inlet, outlet, and filter therebetween, and a valve. In certain embodiments, the valve has at least one open position and at least one closed position.

In any of the preferred embodiments, the system provided by the invention includes flow lines that permit the flow of a fluid and/or gas therethrough.

Accordingly, in a preferred embodiment, the system for the seeding, culture, storage, shipping, and/or testing of a cell or tissue graft includes a cellular isolate fluid container; a flow channel disposed between the cellular isolate fluid container, a collection fluid container, an elution fluid container, and a seeding container, wherein the flow channel includes an inlet, an outlet and a filter there between, wherein the filter is adapted to allow flow in at least two directions, and wherein the flow channel is selectively in fluid communication with each of the cellular isolate fluid container; the collection fluid container, the elution fluid container, and the seeding container, respectively; and wherein the seeding container includes a seeding assembly.

In one embodiment, the seeding assembly includes a perforated mandril, and a biocompatible three-dimensional scaffold that is apposed to at least a portion of the mandril. In another embodiment, the system includes at least one residual seeded cell fluid container, wherein the residual seeded cell fluid container is selectively in fluid communication with the seeding container.

In another embodiment, the system includes a vacuum source in fluid communication with the residual seeded cell fluid container.

In certain embodiments, the system is disposable. The closed disposable system allows for a procedure for the construction of tissue engineered graft, e.g., a vascular graft, that can be performed rapidly while achieving similar seeding efficiency as compared to previously described methods (Matsumura, et al., *Biomaterials* 2003; 24:2303-8; and FDA IDE 14127), which are incorporated herein by reference in their entirety. In addition, the use of the system allows one to construct the tissue engineered graft, e.g., vascular graft, at the point of care (i.e., in the operating room precluding the need for scaffold transport.

2. Fabrication of TEVG Seeding Systems

Figures 1B, 1C, 1D, 1E, 1F, 1G:
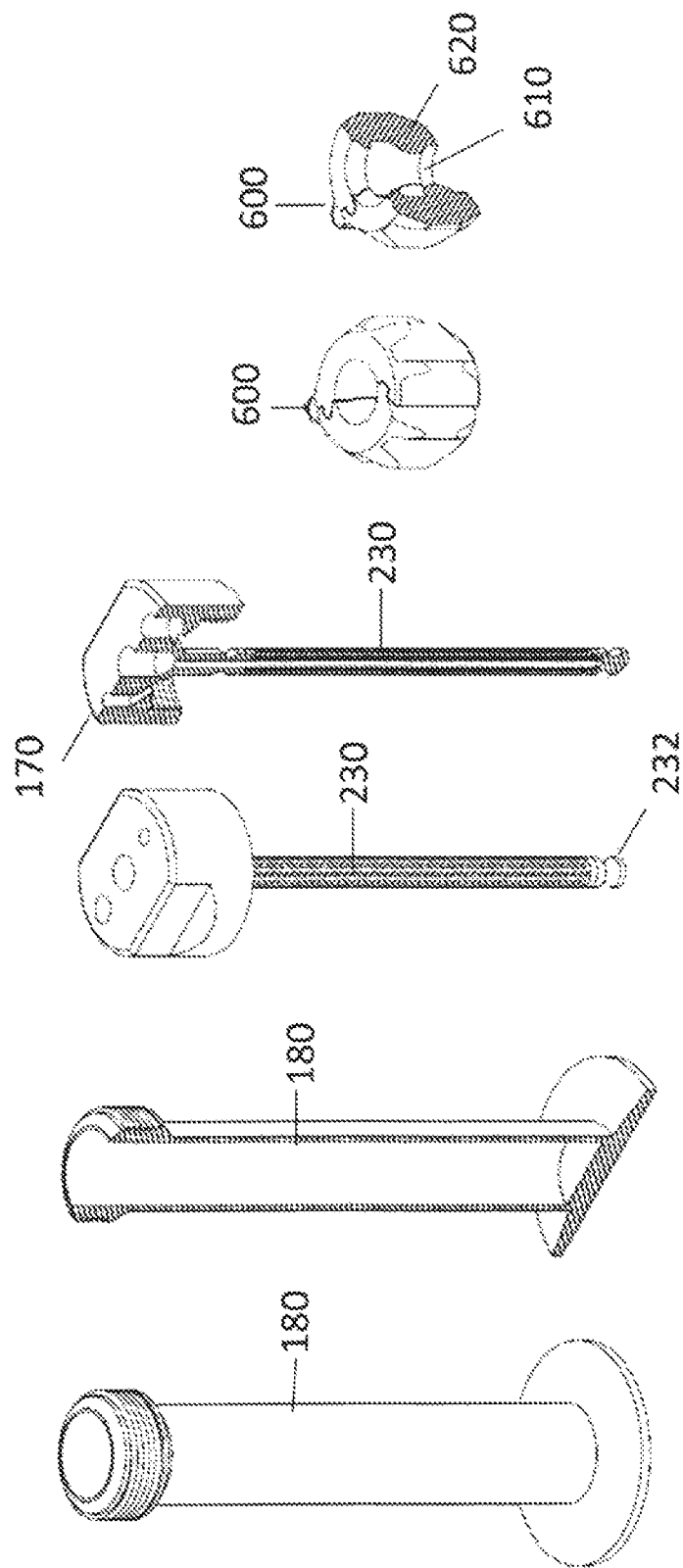
FIG. 1B is a drawing illustrating a perspective view of an advanced seeding chamber (180) that can be used in place of the seeding chamber (18) shown in FIG. 1A.
FIG. 1C is a drawing illustrating a cross-sectional perspective view of the seeding chamber (180) that can be used in place of the seeding chamber (18) shown in FIG. 1A.
FIG. 1D is a drawing illustrating a perspective view of the suction rod (230) containing an integral threaded top (170) that can be used in place of the seeding chamber (18) shown in FIG. 1A.
FIG. 1E is a drawing illustrating a cross-sectional perspective view of the suction rod (230) containing an integral threaded top (170), and also containing an indent at the base (232) configured to receive a correspondingly shaped clip (600). A similar indent is provided at the top of the suction rod.
FIG. 1F is a drawing illustrating a perspective view of a clip (600), that can be used in place of the O-ring (22) within the seeding chamber (100) shown in FIG. 1A. The clip (600) is typically hollow, having a solid wall (620), surrounding a hollow center (610). Optionally the wall (620) contains a hinge to facilitate opening and closing of the clip (600).
FIG. 1G is a drawing illustrating a cross-sectional perspective view of a clip (600) within the seeding chamber (100) shown in FIG. 1A.
Figure 1H:
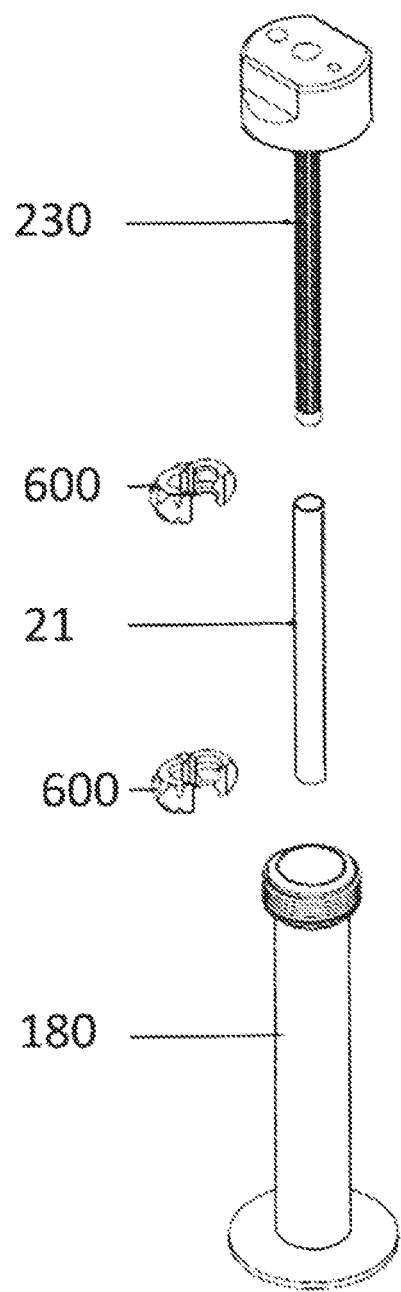
FIG. 1H is an exploded view illustrating the assembly of the different components of a seeding chamber assembly (200), that can be used in place of the seeding chamber assembly (100) shown in FIG. 1A, including the suction rod (230), scaffold (20), scaffold clips (600) and seeding chamber (180).

In a preferred embodiment one or more of the component parts of the seeding system are custom designed such that the assembly is optimally sized to accommodate the dimensions of the patient-specific TEVG. Preferably, the system, or parts of the system are fabricated using 3D printing of suitable materials. In an exemplary embodiment, one or more of the component parts of the seeding chamber of the system illustrated in FIG. 1A is fabricated by 3D printing of suitable materials. In a particular embodiment, the components that are 3D-printed include one or more of a seeding chamber (180) (FIGS. 1B, 1C), a suction rod (230) (FIGS. 1D, 1E), and a clip (600) optionally having a living hinge (FIGS. 1F, 1G). The components can be assembled into a seeding chamber assembly (100) (FIGS. 1I, 1J), when assembled with a manufactured scaffold (21) (FIG. 1H). The dimensions of the component parts of the seeding system can be varied according to those desired, for example, by the dimensions of the patient-specific vascular graft.

In an exemplary embodiment, the seeding chamber base has a radius of between 10 and 100 mm, for example, 33 mm. In an exemplary embodiment, the top of the seeding chamber has a diameter of between 10 and 100 mm, for example, 38.1 mm. In an exemplary embodiment, the seeding chamber base has a height of between 20 and 1000 mm, for example, 180 mm. Typically, the inner diameter of the seeding chamber aperture is between 5 and 90 mm, for example, 25.86 mm. A typical thickness for the wall of the seeding chamber is between 0.5 and 10 mm, for example, approximately 2 mm. When the seeding chamber has a threaded top, the height of the threaded section is typically approximately 10% of the total length of the chamber, for example, 20.55 mm. The mandril (20), seeding tube (18), and one or more scaffold clips (60) are typically sized corresponding to the desired size of the vascular graft (21). seeding chamber, and are sized to fit together within the seeding chamber. is typically sized according to the corresponding sized seeding chamber. In an exemplary embodiment, the length of the mandril that will fit within a 180 mm long seeding chamber is about 128 mm.

Figure 1I:
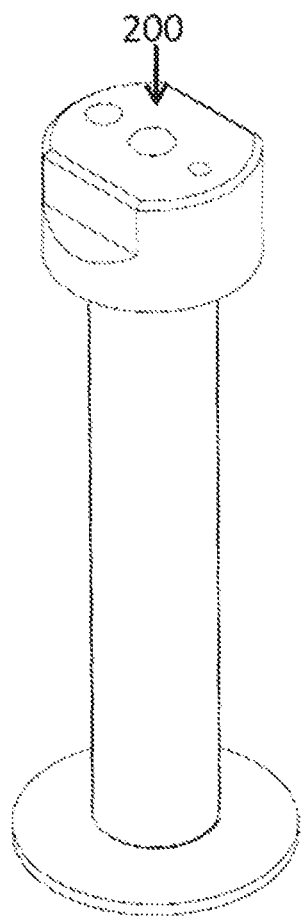
FIG. 1I is a drawing illustrating a perspective view of the assembled seeding chamber assembly (200) shown in FIG. 1H.
Figure 1J:
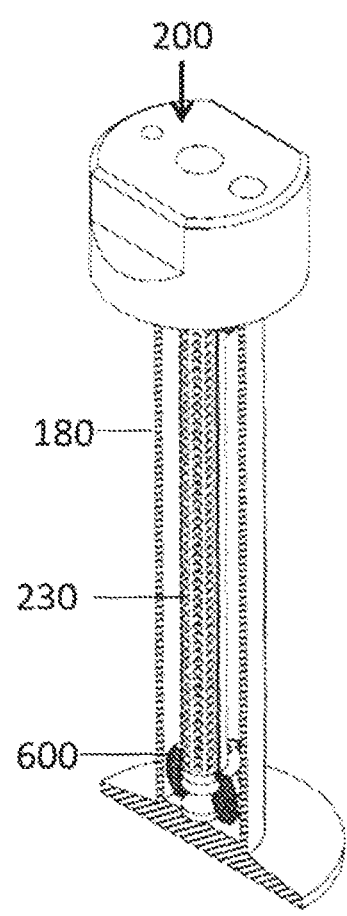
FIG. 1J is a drawing illustrating a partial cross-sectional view of the seeding chamber assembly (200) shown in FIG. 1I.

In some embodiments, the dimensions of the patient-specific mandrel are used to enable the computer-assisted design of the dimensions of the seeding chamber (180) and corresponding component parts of the seeding chamber assembly (100) (FIGS. 1I, 1J), including a suction rod (230) and threaded cap (170) (FIGS. 1D, 1E), a scaffold-specific mandrel (20), a scaffold fastener, or clip (600) (FIGS. 1F, 1G) and a seeding chamber (180) (FIGS. 1B, 1C). In preferred embodiments, all of the component parts of the seeding chamber of the seeding system are produced by a method of 3D printing. The 3D-printed components of the assembly can be assembled with the scaffold or graft (21) (e.g., according to the schematic in FIG. 1H) to produce the custom-designed seeding chamber assembly (100) (FIGS. 1I, 1J).

Suitable materials for 3D printing of TEVG Seeding Systems include polymers and metals, including, but not limited to, stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. In some embodiments, the mandrel is made of a liquefiable material, thereby allowing the release of the mandrel from the graft in an easy fashion. The use of liquefiable mandrels also allows for forming complex shapes of the graft. Typically, fabrication of custom-designed mandrel models is carried out in a small amount of time, such that patient-specific grafts can be produced within one week of surgery, or less, within one, two, three, four, five or six days of surgery.

B. Methods for Seeding TEVG Grafts in a Closed System

The system (see FIG. 1A) allows for the isolation of bone marrow-derived mononuclear cells, and, while maintaining an aseptic system, or while maintaining a closed sterile system, seeding the cells onto a biocompatible three-dimensional scaffold, which after a brief period of incubation (e.g., about three hours or less, more preferably, about two hours or less) can be used as a tissue engineered vascular graft.

The system can be used as an aseptic system, wherein a sterile seeding container is assembled using aseptic techniques, in a sterile field, such as the operating room, using sterile gloves to handle the components. The assembled seeding container can be connected to the other components of the system pre-assembled in a closed sterile manner.

Alternatively, and preferably, the system can be used while maintaining a closed sterile system, wherein the system has been pre-assembled and sterilized before use.

Advantages of this technology include that it enables the assembly of a tissue engineered construct without the need for sterile hood or ISO Class 7 room dramatically reducing the cost for producing tissue engineered products while simultaneously increasing the clinical utility of the use of the tissue engineered product by precluding the need for such equipment or facilities. Another advantage is that it provides a graft in less time that previously available.

In a preferred embodiment, the fluid is removed from the seeding container by a vacuum, e.g., −20 mm Hg (or another suitable value less than the bubble point of the filter in the flow channel 2), which is applied until all of the cell suspension has passed through the scaffold and is collected in the residual seeded cell fluid containers 35a, 35b.

In another embodiment, a housing includes the flow channel, including an inlet, outlet, and filter. In another embodiment the housing includes the flow channel, inlet, outlet, and filter therebetween, and a valve. In certain embodiments, the valve has at least one open position and at least one closed position.

Referring to FIG. 1A, (i) a bone marrow aspirate (e.g., 5 cc/kg body weight) is aseptically collected and injected into cell isolate fluid container (3); (ii) using a vacuum, the bone marrow aspirate is passed through a flow channel (7) including a filter which traps the bone marrow derived-mononuclear cells as the aspirate passes from the upstream surface of the filter medium and through the downstream surface of the filter medium; (iii) the remaining portion of the bone marrow aspirate (which is typically composed primarily of plasma, but may include red blood cells and/or platelets) is collected in collection fluid container (13); (iv) the elution solution in elution fluid container (9) is passed through the flow channel (7), wherein the elution solution passes from the downstream surface of the filter medium and through the upstream surface of the medium, and into a seeding container (18) such that the filter releases the bone marrow-derived mononuclear cells which are collected in the seeding container; (v) the seeding container (18) contains a scaffold that is inserted over a perforated mandril (20); (vi) the bone marrow-derived mononuclear cell suspension fills the seeding container (18) completely covering the scaffold that is inserted over the perforated mandril (20); (vii) a vacuum (e.g., −20 mm Hg) is applied until all of the cell suspension has passed through the scaffold and is collected in at least one residual seeded cell fluid container (35a, 35b); and (viii) the filtered bone marrow aspirate, typically primarily comprising plasma, is passed, using flow induced by a vacuum, from the collection container (13), into seeding container (18), which contains the seeded scaffold, thus bathing the seeded scaffold.

In another embodiment, the method includes collecting a bone marrow aspirate (e.g., 5 cc/kg body weight), aseptically, into container 3, wherein at least valve 51 is closed (typically, one or more of valves, 6, 7, 8, 10, and 15 are also closed). Clamps 5 and 10 are opened, and, using a vacuum, the bone marrow aspirate is passed (via fluid lines 51 and 52) through the flow channel 7 filter, which traps the bone marrow derived-mononuclear cells. The remaining portion of the bone marrow aspirate (typically, composed primarily of plasma) is collected (via fluid lines 53 and 54 and port 11) in collection fluid container 13. Subsequently, clamps 5 and 10 are closed, valves 8 and 6 are opened, and the elution solution is passed (via fluid lines 55 and 53) through the filter 7 releasing the bone marrow-derived mononuclear cells which pass through fluid lines 52, 56, and 57 and port 16 and are collected in the seeding container 18. The seeding container (18) contains the seeding assembly (100), including the scaffold 21 that is inserted over a perforated porous tube/mandril (20). In a preferred embodiment, the bone marrow-derived mononuclear cell suspension fills the seeding container 18 completely covering the scaffold (21) that is inserted over the perforated mandril (20). Subsequently, valves 6 and 10 are closed, and valve (27) is opened, and a vacuum (e.g., −20 mm Hg) using a vacuum assembly including a regulator 28, is applied until all of the cell suspension has passed through the scaffold and is collected, via port 24 and fluid line 58a in residual seeded cell fluid container 35a (if there is excess fluid, the additional cell suspension is collected, via fluid line 58b, in residual seeded cell container 35b).

After vacuum has ceased, valve 27 is preferably closed, valve 15 is opened, and the serum in container 13 is drained, preferably using a vacuum, via fluid lines 59 and 57 and port 16 into seeding container 18 thus bathing the seeded scaffold. If the optional vent 26 is included as part of the seeding container 18, gas exchange may occur, e.g., during bathing. If desired, e.g., for ease of handling the seeding container and/or the seeding container components (such as the mandril and/or scaffold) while the cells are being bathed, one or more system components upstream of the seeding container 18, such as filter 7, elution container 9, collection container 13, and/or the cellular isolate container 3 can be removed (e.g., after heat sealing the appropriate fluid line) and discarded.

Figure 3:
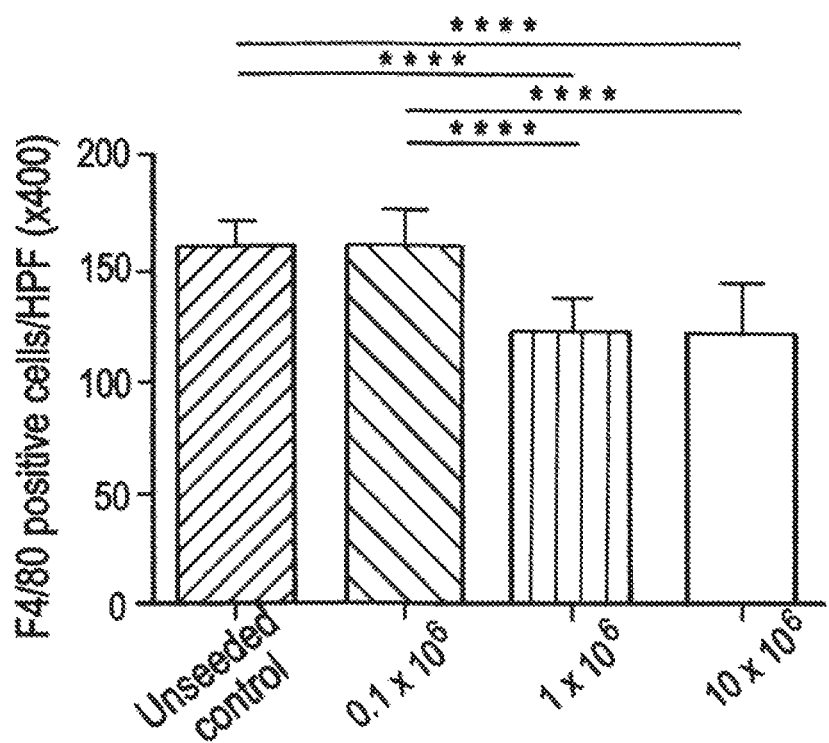
FIG. 3 is a histogram showing F4/80 Positive Cells/HPF ($\times 400$) (0-200), over Cell Seeding Dose ($\times 10^6$) for each of unseeded (control) sample, and samples seeded with 0.1, 1.0 and $10.0 \times 10^6$ cells, respectively ($p<0.0001$).

As an additional option, the entire apparatus is placed in an incubator at, e.g., approximately 10-100% humidity, 35-37°, with 3-5% $CO_2$) for approximately two hours after which the seeded scaffold can be aseptically removed from the container (e.g., after removing the cap 17 (FIG. 1A) or after cutting open the flexible container (FIG. 3)) and used as a tissue engineered vascular graft.

V. Methods of Use of TEVGs Seeded with Cells

Patient-specific TEVG seeded with cells can reduce or prevent the rate of post-operative stenosis of the TEVG, relative to the rate of stenosis in the equivalent TEVG in the absence of cells. Therefore, patient specific TEVG can be seeded with an effective amount of cells to reduce or prevent one or more of the immune processes associated with development of post-operative stenosis, including inflammation.

Tissue repair has four distinct stages, including: a) clotting/coagulation; b) inflammation; c) fibroblast migration/proliferation; and d) a final remodeling phase where normal tissue architecture is restored. In the earliest stages after tissue damage, epithelial cells and/or endothelial cells release inflammatory mediators that initiate an antifibrinolytic-coagulation cascade that triggers clotting and development of a provisional extracellular matrix (ECM). Aggregation and subsequent degranulation of platelets promotes blood vessel dilation and increased permeability, allowing efficient recruitment of inflammatory cells such as neutrophils, macrophages, lymphocytes, and eosinophils to the damaged tissue. Neutrophils are the most abundant inflammatory cell at the earliest stages of wound healing, but are quickly replaced by macrophages after neutrophil degranulation. Activated macrophages and neutrophils debride the wound, eliminate any invading organisms and produce a variety of cytokines and chemokines that amplify the inflammatory response as well as trigger fibroblast proliferation and recruitment. Upon activation, fibroblasts transform into myofibroblasts that secrete α-smooth muscle actin and ECM components. Finally, in the remodeling phase epithelial/endothelial cells divide and migrate over the temporary matrix to regenerate the damaged tissue. Thus, healing and neotissue generation is a finely regulated process that balances the need to regenerate tissue and thicken blood vessel walls, without excessive thickening and stenosis or fibrosis.

Macrophages

It has been shown that the presence of circulating monocytes and infiltrating macrophages is critical for wound healing and neotissue development (Arras, et al., *J Clin Invest*, 101(1): 40-50 (1998)). However, the extent of macrophage infiltration at a site of tissue damage has also been correlated with proliferative dysregulation and neointima formation (Hibino, et al., *FASEB J.* 25(12):4253-63 (2011)). Further, numerous studies have indicated that macrophages and fibroblasts are the main effector cells involved in the pathogenesis of fibrosis (reviewed in Wynn, *Nat Rev Immunol.* 4(8):583-94 (2004)).

Following vascular damage, inflammatory monocyte cells (CD16-hi, CD64-hi and CD14-hi in humans; CD115+, CD11b+ and Ly6c-hi in mice) are recruited to the damaged tissue and differentiate into activated macrophages (Emr1-hi in humans; F4/80-hi in mice) upon exposure to local growth factors, pro-inflammatory cytokines and microbial compounds (Geissmann et al., *Science* 327: 656-661 (2010)). Excessive macrophage infiltration results in stenosis, whilst complete inhibition of macrophage infiltration prevents neotissue formation (Hibino, et al., *FASEB J.* 25(12):4253-63 (2011).

Two distinct states of polarized activation for macrophages have been defined: the classically activated (M1) macrophage phenotype and the alternatively activated (M2) macrophage phenotype (Gordon and Taylor, *Nat. Rev. Immunol.* 5: 953-964 (2005); Mantovani et al., *Trends Immunol.* 23: 549-555 (2002)). The role of the classically activated (M1) macrophage is an effector cell in TH1 cellular immune responses, whereas the alternatively activated (M2) macrophage appears to be involved in immunosuppression and wound healing/tissue repair. M1 and M2 macrophages have distinct chemokine and chemokine receptor profiles, with M1 secreting the TH1 cell-attracting chemokines CXCL9 and CXCL10, and with M2 macrophages expressing chemokines CCL17, CCL22 and CCL24.

The presence of M2 macrophages has been associated with neo-intima development and stenosis (Hibino, et al., *FASEB J.* 25(12):4253-63 (2011)). The correlation between the extent of macrophage infiltration, neotissue formation and stenosis at certain time points following tissue graft implantation provides means to prevent stenosis through modulation of macrophage activity.

Further, macrophages are typically located close to collagen-producing myofibroblast cells, and it has been shown that monocyte-derived macrophages critically perpetuate inflammatory responses after injury as a prerequisite for fibrosis (Wynn and Barron, *Semin Liver Dis* 30(3):245-257 (2010)). Macrophages produce pro-fibrotic mediators that activate fibroblasts, including platelet-derived growth factor (PDGF), a potent chemotactic agent, and transforming growth factor beta (TGF-B). Specifically, a marked increase of the non-classical M2 (CD14+, CD16+) subset of macrophages has been correlated with pro-inflammatory cytokines and clinical progression in patients suffering from chronic liver disease. During fibrosis progression, monocyte-derived macrophages release cytokines perpetuating chronic inflammation as well as directly activate hepatic stellate cells (HSCs), resulting in their proliferation and trans-differentiation into collagen-producing myofibroblasts (Zimmermann, et al., *PLOS One*, 5(6):e11049 (2010)).

Platelets

Aggregated platelets assist the repair of blood vessels by secreting chemicals that attract fibroblasts from surrounding connective tissue into the wounded area to heal the wound or, in the case of dysregulated inflammatory responses, form scar tissue. In response to tissue injury, platelets become activated and release a multitude of growth factors which stimulate the deposition of extracellular matrix, such as platelet-derived growth factor (PDGF), a potent chemotactic agent, as well as transforming growth factor beta (TGF-β). Both of these growth factors have been shown to play a significant role in the repair and regeneration of connective tissues. PDGF functions as a primary mitogen and chemoattractant which significantly augments the influx of fibroblasts and inflammatory cells, as well as stimulating cell proliferation and gene expression. PDGF enables leukocytes to firmly attach to the vessel wall and finally to transmigrate into the subendothelial tissue. However, the platelet-derived chemokines are also known to induce smooth muscle cell (SMC) proliferation and play a role in neointimal proliferation and organ fibrosis (Chandrasekar, et al., *J Am College Cardiology*, Vol 35, No. 3, pp. 555-562 (2000)). Increased expression of PDGF and its receptors is associated with scleroderma lung and skin tissue. Specifically, there is evidence for an autocrine PDGF-receptor mediated signaling loop in scleroderma lung and skin fibroblasts, implicating both TGF-β and PDGF pathways in chronic fibrosis in scleroderma (Trojanowska, *Rheumatology*; 47:v2-v4 (2008)). In addition, deregulation of PDGF signaling is associated with cardiovascular indications such as pulmonary hypertension, and atherosclerosis.

Media layer smooth muscle cell (SMC) proliferation and migration in response to injury-induced PDGF are essential events contributing to neointimal thickening (Fingerle, et al., Proc Natl Acad Sci., 86:8412 (1989); Clowes, et al., Circ. Res., 56:139-145 (1985)) which eventually leads to blood vessel narrowing and stenosis.

Other healing-associated growth factors released by platelets include basic fibroblast growth factor, insulin-like growth factor 1, platelet-derived epidermal growth factor, and vascular endothelial growth factor.

Patient-specific TEVG can be seeded with an effective amount of cells to create a pro-regenerative immune environment that enhances wound healing and prevents restenosis. Patient-specific TEVG can also be seeded with an effective amount of cells to modulate platelet activity and function. Thus, patient-specific TEVG can also be seeded with an effective amount of cells to reduce or prevent the biological functions of platelets, such as platelet aggregation and the production/expression of platelet derived growth factor (PDGF).

Methods of using the described patient-specific tissue engineering vascular grafts seeded with cells to reduce post-operative stenosis of the graft include surgically implanting, or otherwise administering the cell-seeded grafts to within a patient. Typically, the method of implanting includes attaching the graft to a section of an artery that is to be replaced or augmented. Methods of attaching vascular grafts are known in the art. The methods typically reduce or inhibit the infiltration of macrophage cells, or the conversion of macrophage cells from M1 to M2 phenotype, or both, compared to a control, such as an equivalent graft that is not seeded with cells, or seeded with fewer cells. In some embodiments, the methods reduce or inhibit proliferation of macrophage cells without reducing or inhibiting vascular neotissue development. A subject can have stenosis, restenosis or other vascular proliferation disorders, or be identified as being at risk for restenosis or other vascular proliferation disorders, for example subjects who have undergone, are undergoing, or will undergo a vascular trauma, angioplasty, surgery, or transplantation arteriopathy, etc. Any of the methods described can include the step of identifying a subject in need of treatment.

The present invention will be further understood by reference to the following non-limiting examples.

EXAMPLES

Example 1: 3D Printing a Closed, Disposable Seeding System for Rapid Preparation of Patient Specific Tissue Engineered Vascular Grafts Materials and Methods Study Design The first FDA approved tissue engineered vascular graft (TEVG) for the palliation of congenital cardiac anomalies is prepared via an open technique in an ISO-Class 7 clean room. Autologous bone marrow mononuclear cells (BMMNCs) are enriched by density gradient centrifugation and subsequently vacuum seeded onto a biodegradable tubular scaffold. Autologous bone marrow mononuclear cells (BM-MNCs) are enriched by density-gradient centrifugation and subsequently vacuum seeded onto a biodegradable tubular scaffold. However, the time, labor, and resource-intensive nature of graft preparation along with the complexities of maintaining a GMP-compliant clean room limit the widespread adoption of this approach.

Attempts to optimize scaffold seeding have resulted in the development of a filter-based system for BM-MNC isolation and a closed, disposable seeding device, which have previously been validated in small and large animal models. Integration of pre-operative imaging studies, computational hemodynamic modeling, computer-aided design, and 3D printing allow for the creation of an optimal patient-specific TEVG scaffold and closed seeding system. An improved single-use TEVG seeding prototype fabricated by 3D printing that is suitable for preclinical evaluation is described.

Design Criteria

The design of the scaffold seeding system is carried out to meet criteria including a cost-effective device design; fabrication in under 36 hrs, use of only FDA approved materials, ability to sterilize the system, integration with pre-existing filters, such as the PALL LEUKAHARVEST®, sampling parts to monitor clinical TEVG release criteria, DICOM-compatible design workflow, easily tunable for diverse anatomical requirements, and to minimize scaffold handling.

3D Printing

A prototype 3D printed closed disposable seeding system was designed and printed using a 3D-printer. A pre-operative MRI imaging of a candidate TEVG recipient with dextrocardia, transposed great arteries, and total anomalous pulmonary venous return (APVR) status post-TAPVR repair and right-sided bidirectional Glenn shunting was used to design a patient-specific seeding system. A commodity fused deposition modeler (Ultimaker 2) was used to print the components of the seeding system from poly-lactic acid filament, over the course of 36 hrs.

Components that are printed include a suction rod, a custom-designed mandrel, a scaffold, a scaffold fastener, and a seeding chamber.

Assembly of 3D-Printed Seeding System

Assembly of the seeding system following 3D-printing of the component parts is carried out according to the steps of threading the suction rod onto the scaffold-specific mandrel, placing the scaffold onto the mandrel, creating an air-tight seal using the air-tight fastener, threading the mandrel and the scaffold onto the seeding chamber, and then seeding the scaffold by applying a vacuum through the chamber.

Results

The patient specific graft is significantly different from the currently used scaffold in that it is nonlinear, there is a gradual internal diameter increase of 3.0 mm, and its overall length is greater than the clinically used graft (13 cm). The differences highlight the advantages and utility of the patient-specific approach. CAD renderings of the custom scaffold and closed, single use seeding system allow for rapid in silico prototyping and 3D printing.

This complex case represents a situation in which the ideal vascular conduit would not be the currently utilized linear graft of constant diameter, and highlights the advantages and feasibility of the approach. Translation of the 3D-printed closed disposable seeding system to the clinic would allow for an off-the shelf patient-specific TEVG for point-of-care treatment of congenital heart diseases.

Example 2: Rational Design of an Improved Tissue Engineered Vascular Graft

Materials and Methods

Study Design

To optimize the TEVG assembly and increase the patency of the TEVG, studies were carried out to determine optimal parameters including cell seeding dose, and graft incubation time after seeding. Studies investigating the effect of cell seeding dose and incubation time on tissue engineered vascular graft (TEVG) patency determined that increasing the BM-MNC dose and reducing incubation time is a viable strategy for improving the performance and utility of the graft.

Various doses of bone marrow-derived mononuclear cells (BM-MNCs) were seeded onto TEVGs, incubated for 0 or 12 hours, and implanted in C57BL/6 mice. Different doses of human BM-MNCs were seeded onto TEVGs and measured for cell attachment. To optimize the TEVG, a murine model to investigate the cellular and molecular mechanisms underlying vascular neotissue formation in the TEVG was developed (Roh, et al. *Biomaterials*. 29(10), 1454-1463 (2008)).

Bone Marrow Harvesting and Seeding for Mouse Graft

Bone marrow was collected from the femurs and tibias of syngeneic C57BL/6 mice and mononuclear cells were isolated using the density centrifugation method (Lee, et al. *J Vis Exp*. (88), (2014)). All animal experiments were approved by the Nationwide Children's Hospital institutional guidelines for the use and care of animals (IACUC).

Determination of Optimal Cell Incubation Time

To determine optimal cell incubation times, $1 \times 10^6$ cells/graft were seeded statically onto biodegradable scaffolds formed from polyglycolic acid sheet with a co-polymer sealant solution of poly-L-lactide and ε-caprolactone, 0.82 mm in inner diameter and 3 mm in length (Gunze Co. Ltd., Kyoto, Japan). Scaffolds were incubated for 0, 0.5, 2 and 12 hours, respectively, in RPMI 1640 (Sigma) at 37° C. in a $CO_2$ incubator.

Determination of Optimal cell Dose

In order to determine the optimal cell dose, four different doses of isolated mononuclear cells were seeded statically, 0.0, $0.1 \times 10^6$, $1 \times 10^6$, and $10 \times 10^6$ cells/graft, respectively, and incubated overnight. After the incubation, grafts were used either for cell counting using a DNA assay (n=6/group) to quantify cell attachment to the scaffold or implanted onto mice as an inferior vena cava (IVC) interposition graft (n=25/group) (Lee, et al. *J Vis Exp*. (88), (2014)).

Cell Source and Seeding for Human Graft

Human bone marrow was purchased from Lonza (Lonza Walkersville Inc., Walkersville, Md.). Three different doses of bone marrow (BM) were used in this study, 12.5, 25, and 50 mL/graft (n=5, 7, 8, respectively). After filtering BM through 100 μm filters, the BM-MNCs were isolated by a density centrifugation method (Udelsman, et al. *Tissue Eng Part C Methods*. 17(7), 731-736 (2011)). After counting the total number of isolated BM-MNCs, the cells were then seeded onto biodegradable scaffold (18 mm in diameter and ~120 mm in length, provided from Gunze) using the vacuum seeding method (Udelsman, et al. *Tissue Eng Part C Methods*. 17(7), 731-736 (2011)) and incubated for 2 hours similarly to currently ongoing clinical trial (IDE 14127). The scaffold was cut into 5 $mm^2$ sections and cell attachment was quantified using a DNA assay.

In Vitro DNA Assay

Cell attachment onto the TEVG scaffolds was determined by measuring DNA content using the fluorimetric QUANT-IT™ PICOGREEN® dsDNA Assay Kit (Life Technologies, Grand Island, N.Y.) following the manufacturer's instructions. The QUANT-IT™ PICOGREEN®dsDNA reagent is a fluorescent nucleic acid stain for the quantification of double stranded DNA in solution. After lysing the cells attached to the scaffold, the bound stain in dsDNA was detected using a fluorescence microplate reader. A standard curve of cell number as a function of fluorescence was generated using known quantities of human BM cells, and the number of cells seeded onto each scaffold was determined. Briefly, the number of attached cells/area was calculated by dividing the total attached cell numbers over the luminal surface area and was expressed as $10^3$ cells/$mm^2$ area, and seeding efficiency was calculated by dividing the attached cells/area by the seeded cells/area (Udelsman, et al. *Tissue Eng Part C Methods*. 17(7), 731-736 (2011)).

Surgical Implantation

The grafts were implanted as IVC interposition grafts onto 6-8 week old female C57BL/6 mice as described previously (Lee, et al. *J Vis Exp*. (88), (2014)). Briefly, after induction of anesthesia (Ketamine, 100 mg/kg; xylazine 10 mg/kg; ketoprofen 5 mg/kg as analgesic, Intraperitoneal) a midline laparotomy incision was made and the aorta and IVC were bluntly separated. Two microclamps were placed on both sides of the aorta and IVC, and then the IVC was transected. The TEVG was implanted as an end-to-end IVC interposition graft using 10.0 prolene sutures. The TEVGs were harvested 2 weeks after implantation. Freshly harvested samples were perfusion fixed with 10% formalin and used for histology and immunohistochemistry.

Histology and Immunohistochemistry

Explanted TEVGs were fixed in 10% neutral buffered formalin overnight, embedded in paraffin, and sectioned (4 μm thick sections) as described previously (Roh, et al. *Biomaterials*. 29(10), 1454-1463 (2008)). Sections were stained with hematoxylin and eosin (H&E), Hart's, Masson's Trichrome, and Alcian blue. Macrophages, MMP-2, and MMP-9 were identified via immunohistochemistry. Following de-paraffinization, rehydration, and blocking for endogenous peroxidase activity and nonspecific background staining, sections were incubated with the following primary antibodies: rat anti-F4/80 (1:1000, AbD Serotec, Oxford, UK), rabbit anti-MMP-2 (1:200, Abcam, Cambridge, UK), and rabbit anti-MMP-9 (1:200, Abcam). Primary antibody binding was detected by incubation with species appropriate biotinylated secondary antibodies, namely, goat anti-rat IgG (1:200, Vector Laboratories, Burlingame, Calif.), and goat anti-rabbit IgG (1:200, Vector) respectively, followed by binding of horseradish peroxidase streptavidin (Vector) and subsequent chromogenic development with 3,3-diaminobenzidine (Vector). Nuclei were counter-stained with hematoxylin (Gill's Formula, Vector). Light field images were obtained with a Zeiss Axio Imager A2 microscope. Immunofluorescent staining was used to identify endothelial cells (EC) and smooth muscle cells (SMC). Slides were incubated overnight with a primary antibody solution of rabbit anti-CD31 (1:50, Abcam) and mouse anti-human smooth muscle actin ($\alpha$-SMA, 1:500, Dako, Carpinteria, Calif.) which cross-reacts with mouse $\alpha$-SMA. Antibody binding was detected with Alexa Fluor 488® goat anti-rabbit IgG (1:300, Invitrogen, Carlsbad, Calif.) and Alexa Fluor 647® goat anti-mouse IgG (1:300, Invitrogen) secondary antibodies. Cell nuclei were identified by subsequent counterstaining with 4', 6-diamidini-2-phenylindole (DAPI) (Invitrogen). Fluorescent images were obtained with an Olympus IX51 inverted microscope and exposure time was informed by appropriate negative controls.

Quantitative Immunohistochemistry

The number of macrophages infiltrating the TEVG was quantified for each explanted scaffold. Nuclei with positive F4/80 expression were imaged in five equally spaced regions of each section at 400× high power filed (HPF) and counted and totaled using Image J software (National institutes of Health Bethesda, Md.) (Hibino, et al. *FASEB J.* 25(12), 4253-4263 (2011)).

TEVG Morphometry

Graft luminal diameter was measured from H&E stained slides using Image J software. The luminal diameter was determined by dividing the circumference of the lumen by $\pi$. The stenosis rate in the graft was calculated using the ratio between the measured luminal diameter and the original graft luminal diameter. "Critical Stenosis" was defined as a decrease in luminal diameter by more than 75% relative to the original luminal diameter (Hibino, et al. *FASEB J.* 25(12), 4253-4263 (2011)).

Statistical Analysis

One-way analysis of variance (ANOVA) was used to determine differences in cell attachment. Fisher's exact test was used to compare stenosis rate of the grafts. P values less than 0.05 indicated statistical significance. Numeric values are listed as mean±standard deviation.

Results

The incubation time showed minimal effect on TEVG patency. However, seeding the TEVG with cells significantly increased TEVG patency, in a dose-dependent manner. In the human graft, more bone marrow used for seeding resulted in increased cell attachment in a dose dependent manner.

Natural History of Neotissue Formation in the Murine Model

Previous studies demonstrated that TEVG stenosis typically occurs within the first 2-weeks after implantation (Hibino, et al. *FASEB J.* 25(12), 4253-4263 (2011)). At gross observation, the TEVG was partially degraded and significant neotissue formation had occurred at 2 weeks after implantation. Representative histological images of patent and occluded TEVGs indicated that patent TEVGs developed a confluent endothelial cell (EC) layer along the luminal surface and underlying smooth muscle cells (SMC) appeared. In contrast, occluded grafts showed disorganized neotissue formation composed primarily of SMCs embedded in collagen with either an occluded lumen or a narrowed endothelial lined lumen. Both patent and occluded grafts showed early development of elastin, collagen, and glycosaminoglycans, mainly around the remaining grafts. MMP-2 and MMP-9 activities were also observed in the neotissue close to the residual scaffold material suggesting ongoing tissue remodeling.

Duration of Incubation does not Affect TEVG Patency

Figure 2B:
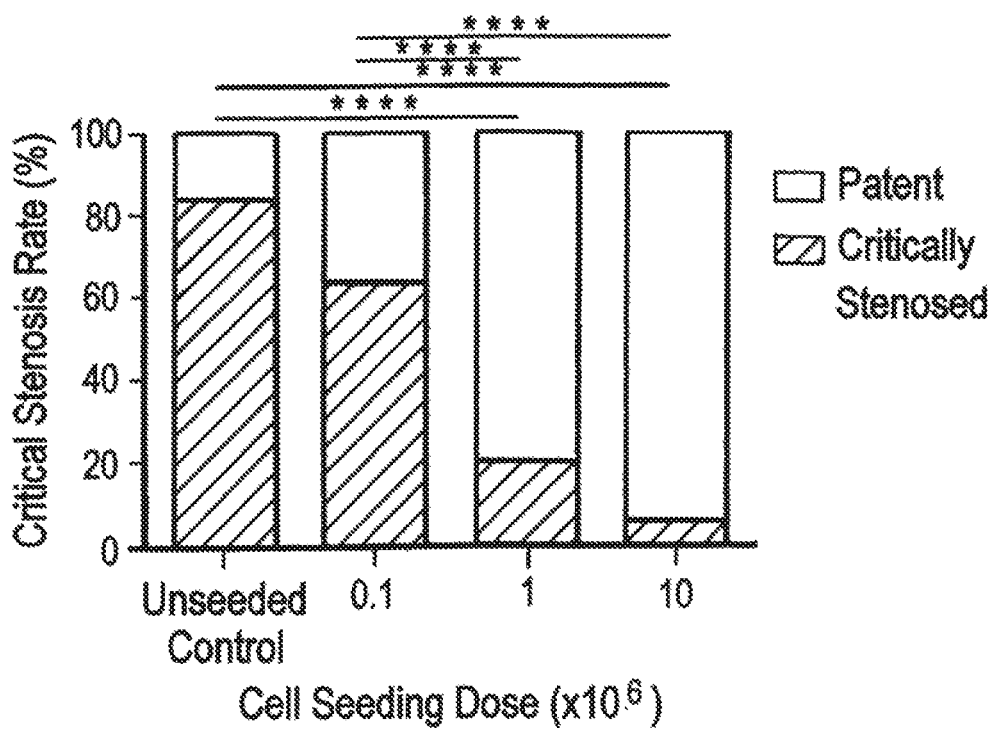

To assess the effect of duration of incubation time on TEVG stenosis, we implanted the $1 \times 10^6$ BM-MNCs seeded TEVG with 0 and 12 hour incubations (n=25/group). The TEVGs were harvested 2 weeks after implantation and the graft patency was compared. The Critical Stenosis rate was significantly higher in the unseeded group than that of both the 0 and 12-hour incubation groups, respectively (84% vs. 12% and 20%, p<0.0001, FIG. 2A). Between the 0 and 12 hour groups, there were no statistical differences, however, the 0 hour group showed slightly increased patency (FIG. 2B). The patency rate in both 0 and 12 hour incubation groups was significantly higher than that of the unseeded control group. Therefore, duration of incubation after cell seeding does not affect TEVG patency.

Cell Seeding Inhibits the Formation of TEVG Critical Stenosis in a Dose Dependent Manner To further investigate the effect of cell seeding dose on the formation of TEVG stenosis, grafts were seeded with $0.1 \times 10^6$, $1 \times 10^6$, or $10 \times 10^6$ cells, respectively, alongside unseeded controls, and were implanted as an IVC interposition graft (n=25/group). At 2 weeks following implantation there was a significant reduction in the stenosis rate in both the $1 \times 10^6$, and the $10 \times 10^6$ cell seeded groups as compared to the unseeded control and $0.1 \times 10^6$ cell seeded groups (20% and 5% vs. 84% and 64%, p<0.0001; FIG. 2B). Seeding grafts with $10 \times 10^6$ cells further decreased the stenosis rate compare to seeding with $1 \times 10^6$ cell, but not significantly (FIG. 2B).

Macrophage Infiltration in TEVG Occurs with a Cell Dose-Dependent Manner

To determine whether cell dose affects macrophage infiltration into the TEVG, the infiltrating macrophages were evaluated by quantitative histological morphometric analysis. The unseeded control and $0.1 \times 10^6$ seeded group showed no statistical differences in infiltrated macrophages, however, the number of macrophages was significantly decreased in both the $1 \times 10^6$ and $10 \times 10^6$ groups (159.05±11.59 and 159.17±16.64 vs. 122.02±14.76 and 120.68±22.91 cells/HPF, p<0.0001, FIG. 3). Thus, similarly to TEVG patency, the numbers of infiltrating macrophages in the unseeded control and $0.1 \times 10^6$ cell seeded group were significantly higher than in both the $1 \times 10^6$ and $10 \times 10^6$ groups.

Duration of Incubation does not Affect Cell Attachment and Seeding Efficiency

To insure the best clinical outcome using TEVG technology, it is important to optimize the time for TEVG assembly, to minimize the time for the surgical procedure, decrease the potential for contamination, and thereby decrease the risk associated with using this technology. Assembling a TEVG as used in the human clinical trial involves the steps of cell harvest and isolation, cell seeding onto the scaffold, and incubating the seeded graft for a period of time (Shin'oka, et al. *J Thorac Cardiovasc Surg.* 129(6), 1330-1338 (2005)). The time required to assemble the TEVG was previously reduced using a closed disposable system that reduced the time for cell isolation and seeding without affecting TEVG patency (Kurobe, et al. *Tissue Eng Part C Methods* 21(1), 88-93 (2015); Kurobe, et al. *Tissue Eng Part C Methods*, (2014)). In the initial human clinical trial, the two hour incubation time was selected arbitrarily, however the optimal incubation time is important to enhance TEVG assembly without affecting patency of the TEVG, as well as for improving safety of the patients.

These studies refine the assembly of the TEVG with a focus on cell dosing and optimal incubation time. The effects of cell dose and duration of incubation on the formation of TEVG stenosis were investigated using a murine model, and results were correlated with the degree of macrophage infiltration, in order to provide insight into the mechanism underlying this process.

To assess the effect of duration of incubation time on cell attachment and seeding efficiency, $1 \times 10^6$ BM-MNCs were seeded onto the biodegradable scaffold and incubated for 0, 0.5, 2, and 12 hours (n=6/group).

Figure 4A:
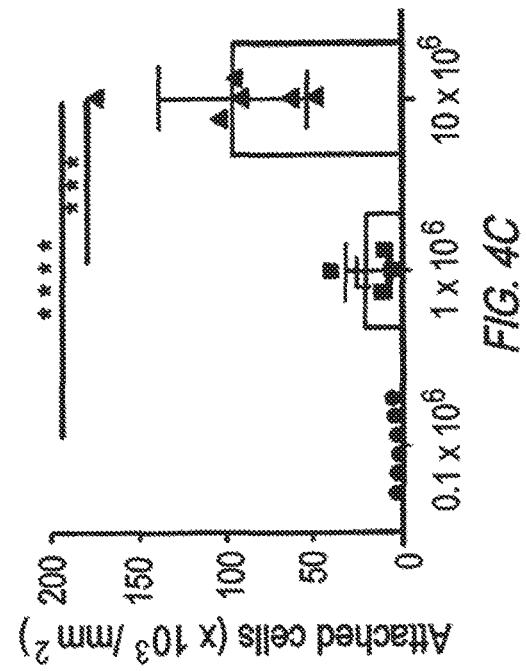
FIG. 4A is a histogram showing Attached Cells (0-60× $10^3$/mm$^2$) over time (hours) for each of samples incubated for 0 hours (●), 0.5 hours (■), 2 hours (▲), and 12 hours (▼), respectively, including the corresponding error bars associated with each of the average values depicted.
Figure 4B:
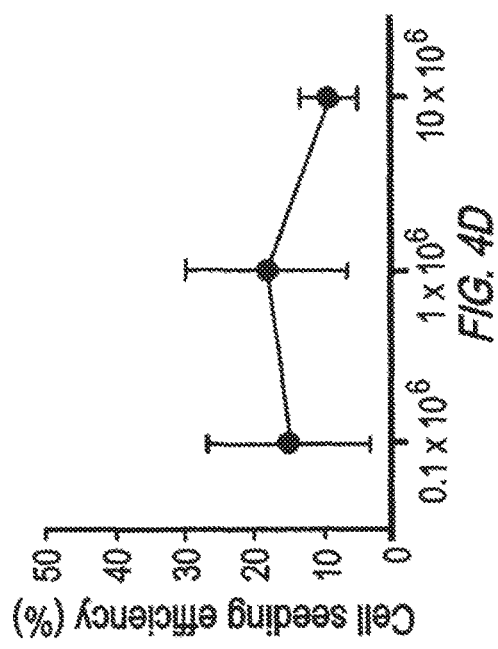
FIG. 4B is a graph showing Cell Seeding Efficiency (0-60%) over time (hours) for each of samples incubated for 0 hours, 0.5 hours, 2 hours, and 12 hours, respectively.
Figure 5A:
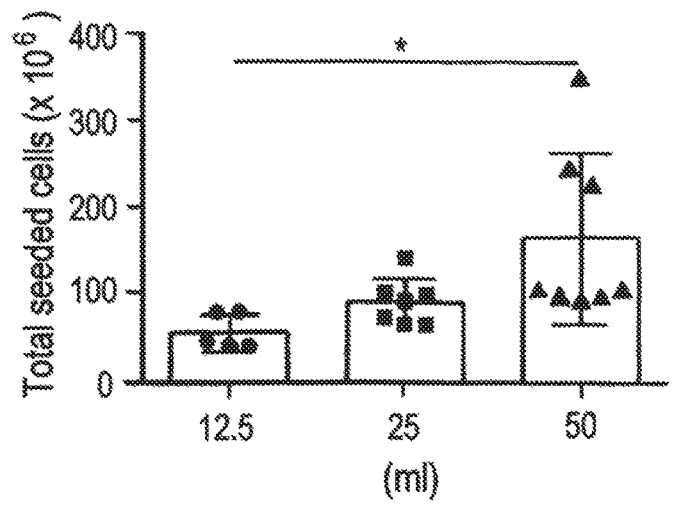
FIG. 5A is a histogram showing Total Seeded Cells (0-400×10$^6$) over volume (ml) for each of 12.5 ml (●), 25 ml (■), and 50 ml (▲) samples, respectively.
Figure 5B:
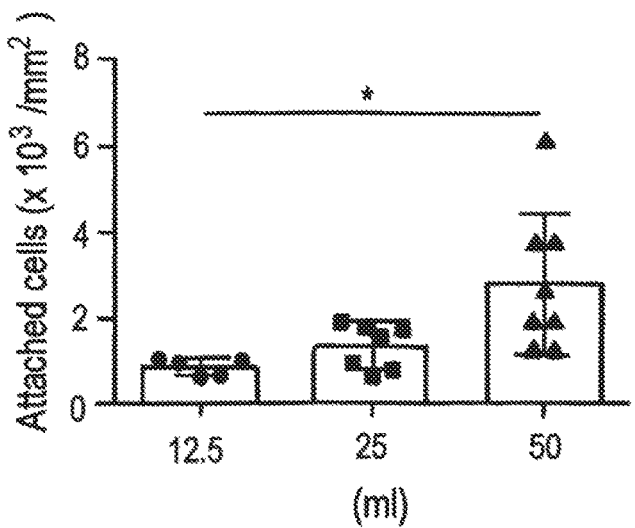
FIG. 5B is a histogram showing Attached Cells (0-8×10$^3$/mm$^2$) over volume (ml) for each of 12.5 ml (●), 25 ml (■), and 50 ml (▲) samples, respectively.

An in-vitro DNA assay for cell counting showed no statistical differences in the number of seeded cells, and seeding efficiency decreased over the duration of incubation time, however, not significantly (FIGS. 4A and 5B).

Figure 4C:
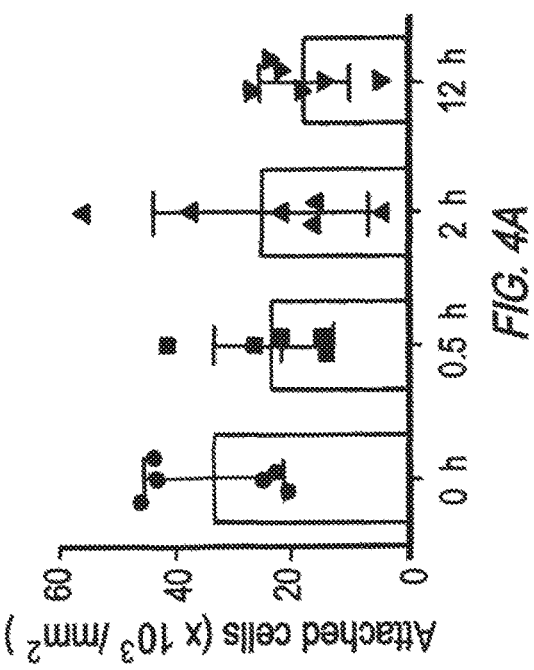
FIG. 4C is a histogram showing Attached Cells (0-200×10$^3$/mm$^2$) for each of samples seeded with $0.1 \times 10^6$ (●), $1.0 \times 10^6$ (■), and $10.0 \times 10^6$ cells (▲), respectively (* $p<0.001$, ** $p<0.0001$).
Figure 4D:
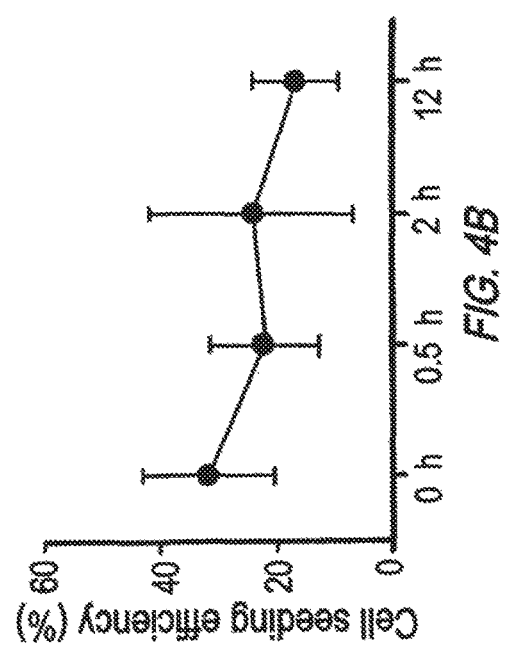
FIG. 4D is a graph showing Cell Seeding Efficiency (0-50%) for each of samples seeded with $0.1 \times 10^6$ (●), $1.0 \times 10^6$ (■), and $10.0 \times 10^6$ cells (▲), respectively.

Cell Attachment and Seeding Efficiency Increase in a Cell Seeding Dose Dependent Manner To determine whether cell seeding dose effected cell attachment and seeding efficiency, biodegradable scaffolds were seeded with $0.1 \times 10^6$, $1 \times 10^6$, and $10 \times 10^6$ BM-MNCs, respectively, and incubated overnight (n=6/group). The $1 \times 10^6$ cell seeded group showed over a 12-fold increase in cell attachment than the $0.1 \times 10^6$ seeded group ($19.09 \pm 13.03 \times 10^3$ vs. $1.56 \pm 1.23 \times 10^3$ cells/mm$^{2'}$ $p<0.001$, FIG. 4C). The $10 \times 10^6$ cell seeded group showed a significant (5-fold) increase in cell attachment compared to the $1 \times 10^6$ cell seeded group, even though 10 times more cells were seeded ($95.85 \pm 48.39 \times 10^3$ vs. $19.09 \pm 13.03 \times 10^3$ cells/mm$^{2'}$$p<0.001$, FIG. 4C). The corresponding cell seeding efficiency in the $10 \times 10^6$ group was also decreased nearly 2-fold relative to both the 0.1 or $1 \times 10^6$ cell seeded groups ($9.16 \pm 4.09$ vs. $14.8 \pm 11.69$ and $18.00 \pm 11.71\%$, FIG. 4D).

Cell Attachment in Human Graft is Also Dose-Dependent Similarly to the Mouse Graft To compare the cell attachment and seeding efficiency from this mouse study to the human clinical study, three different doses of human bone marrow, 12.5 ml, 25 ml, and 50 ml/grafts (n=5, 7, and 8, respectively), were seeded according to the methods used for the human clinical trial (Udelsman, et al. *Tissue Eng Part C Methods*. 17(7), 731-736 (2011)). The total BM-MNCs isolated from each of the 12.5 ml, 25 ml, and 50 ml groups were $57 \pm 21$, $91 \pm 26$, and $165 \pm 96 \times 10^6$ cells, respectively (FIG. 5A). After cell seeding, the attached cells/area was increased in dose-dependent manner. Especially, cell attachment in 50 ml group was significantly more than 12.5 ml group ($2.83 \pm 1.67$ vs. $0.88 \pm 0.21 \times 10^3$ cells/mm$^2$, $p<0.05$, FIG. 5B). The seeding efficiency for all three groups was comparable to that of the mouse graft, which was between 10-20%. The results suggest that increasing the amount of bone marrow harvested from patients would increase BM-MNC attachment in the graft in a dose dependent manner similar to the mouse graft.

Discussion

Experiments to investigate the role of cell dose and duration of incubation were carried out, and strategies for improving the safety and clinical utility of the TEVG were identified. Cell seeding increased TEVG patency in a dose dependent manner, and TEVG patency improved when more cells were seeded, however duration of incubation time showed minimal effect on TEVG patency.

Figure 5C:
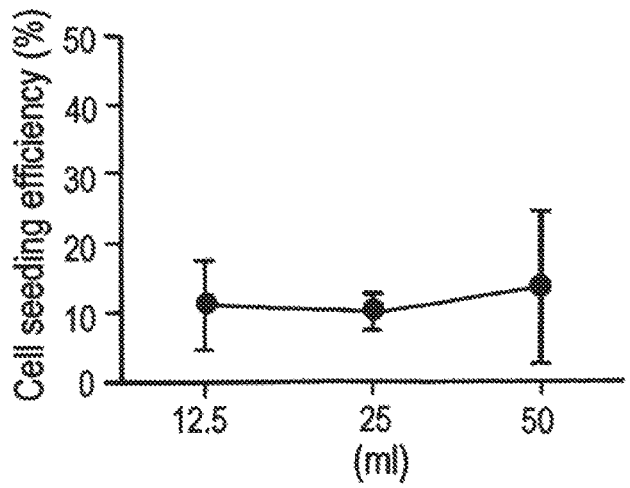
FIG. 5C is a histogram showing Cell Seeding Efficiency (0-50%) over volume (ml) for each of 12.5 ml (●), 25 ml (■), and 50 ml (▲) samples, respectively.

In addition, BM-MNC number and attachment were increased by increasing the amount of bone marrow used for seeding. Based on the data, supra-physiological doses of BM-MNC, i.e., more BM-MNC than can be harvested from a single donor, would saturate the scaffold to the point that additional cell seeding would not significantly increase the number of cells attached to the scaffold (FIGS. 5A-5C).

The dose of cells used to make the TEVG in the human clinical trial was chosen empirically, and represented the number of BM-MNC that could be isolated from 5 ml/kg of bone marrow. From a clinical perspective, up to 20 ml/kg of bone marrow can be harvested from an individual without incurring significant adverse effects and is routinely used for harvesting bone marrow for bone marrow transplantations (Elzouki, et al. Textbook of clinical pediatrics, (Ed.ˆ(Eds). Springer, 3179 (2012)). Increasing bone marrow harvested from a 2.5 kg patient from 5 ml/kg (12.5 ml) to 20 ml/kg (50 ml), would potentially result in a 3 to 4-fold increase of BM-MNCs, and would increase the number of cells attached to the scaffold by approximately 300 to 400% (FIGS. 5A-5C).

Based on the murine study as it relates to the human condition, an estimated 400% increase in cell attachment would result in a 40-80% reduction in incidence of stenosis with the described cell dosing strategy. Further increase in the cell dose is possible, but its use would need to be measured against the increased risk of adverse hemodynamic consequences and the need for transfusion that would be associated with harvesting >20 ml/kg of bone marrow (Elzouki, et al. *Textbook of clinical pediatrics*, (Ed.ˆ(Eds). Springer, 3179 (2012)). Use of growth factors to stimulate bone marrow growth represents an additional strategy for increasing the yield of BM-MNC, and minimizing the amount of time required to assemble the TEVG improves its utility. Assembly can include the processes of isolating BM-MNC; seeding the scaffold; and incubating the seeded construct. The current methodology, based on isolating the BM-MNC using density centrifugation in Ficoll, followed by a 2-hour incubation, requires approximately $268 \pm 9$ minutes to assemble the TEVG (Shin'oka, et al. *J Thorac Cardiovasc Surg*. 129(6), 1330-1338 (2005)).

To reduce the time required for TEVG assembly, a closed disposable system using a filtration/elusion system was previously developed to minimize time for the processes of isolating BM-MNC and seeding (Kurobe, et al. *Tissue Eng Part C Methods*, (2014)). This system offered the potential to drastically minimize times required for cell isolation and seeding, without impacting the patency using a sheep model (Kurobe, et al. *Tissue Eng Part C Methods* 21(1), 88-93 (2015)). However, the results described above indicated that incubation time did not affect the TEVG patency, and the number of cells attached to the scaffold actually decreased with increased periods of incubation. Thus, using the closed apparatus and the reduced incubation period decrease the time required to assemble the TEVG from $268 \pm 9$ minutes to $17 \pm 2$ minutes, further increasing its safety and clinical utility (Kurobe, et al. *Tissue Eng Part C Methods* 21(1), 88-93 (2015)).

Stenosis is a primary graft-related complication. Previous work suggested that graft stenosis is caused by increases in excessive macrophage infiltration and more importantly, cell seeding reduced monocyte/macrophage infiltration and their expression of pro-inflammatory markers (Hibino, et al. *FASEB J*. 25(12), 4253-4263 (2011)). In this study, it was demonstrated that increasing the cell dose reduced the degree of macrophage infiltration, suggesting that the mechanism of action underlying this beneficial effect is immune mediated. These findings are consistent with previous studies demonstrating that cell seeding reduces the degree of host macrophage infiltration and inhibits stenosis compared to unseeded controls. It has also been shown that the time for TEVG incubation does not affect the TEVG patency, enabling a means to minimize the time required for TEVG assembly.

It was revealed that vascular neotissue arises from the ingrowth of endothelial cells and smooth muscle cells from the neighboring blood vessel wall and that, contrary to the classic tissue engineering paradigm, seeded cells do not contribute to vascular neotissue, but instead rapidly disappear after implantation (Roh, et al. *Biomaterials.* 29(10), 1454-1463 (2008); Hibino, et al. *FASEB J.* 25(8), 2731-2739 (2011)). It was also established that vascular neotissue formation is a host macrophage-mediated regenerative process and that cell seeding is not essential for vascular neotissue formation (Hibino, et al. *FASEB J.* 25(12), 4253-4263 (2011)). Conversely, it was previously established that the degree of host macrophage infiltration is directly proportional to the incidence of TEVG stenosis (Hibino, et al. *FASEB J.* 25(12), 4253-4263 (2011)), and that bone marrow mononuclear cell (BM-MNC) seeding inhibits the formation of TEVG stenosis via a TGF-β immune-mediated paracrine effect (Duncan, et al. *J Am Coll Cardiol.* 65(5), 512-514 (2015)). So, although seeding with BM-MNC does not contribute to neotissue formation per se, it does play a role in preventing stenosis and improving patency. These results highlight the importance of BM-MNC seeding.

Example 3: Preclinical Study of Patient-Specific Nanofiber Tissue Engineered Vascular Grafts Using Three-Dimensional Printing in a Sheep Model Materials and Methods
Study Design Tissue-engineered vascular grafts (TEVGs) can overcome limitations of current approaches for reconstruction in congenital heart disease by providing biodegradable scaffolds on which autologous cells proliferate and provide physiologic functionality. However, current TEVGs do not address the diverse anatomic requirements of individual patients. Patient specific TEVGs were therefore constructed using a combining 3D-printing and electrospinning technology.

An electrospinning mandrel was 3D-printed after computer-aided design based on preoperative imaging of the ovine thoracic inferior vena cava. TEVG scaffolds were then electrospun around the 3D-printed mandrel.

Six patient-specific TEVGs were implanted as cell-free inferior vena cava (IVC) interposition conduits in a sheep model and explanted after 6 months for histologic, biochemical, and biomechanical evaluation.

Pre-Surgery Imaging and 3D Model/Mandrel Creation

Based on preoperative angiography images, the diameter and length of the sheep IVC were measured and matching graft models were designed using computer aided design software (Solidworks, Waltham, Mass., USA). The final mandrel design was converted to stereolithography format and exported to Shapeways (NY, USA) for 3D fabrication out of stainless steel (FIGS. 6A-6E).

Scaffold Fabrication

To create the co-electrospun polyglycolic acid (PGA) and polylactide-co-caprolactone (PLCL) scaffolds, 10 wt % PGA was dissolved in hexafluoroisopropanol and 5 wt % PLCL was dissolved in hexafluoroisopropanol. Each solution was stirred via a magnetic stir bar for at least 3 hours at room temperature. In separate syringes, the PGA solution was dispensed at a flow rate of 2.5 mL/hour and the PLCL solution was dispensed at a flow rate of 5.0 mL/hour to create a graft with a 1:1 PGA:PLCL ratio. Both solutions were simultaneously electrospun onto the custom 3D-printed mandrel that was positioned 20 cm from the needle tip and rotated at 30 RPM. A +25 kV charge was applied to each syringe tip and electrospun nanofibers were deposited onto the grounded mandrel until the desired wall thickness was achieved. The electrospun scaffold was then removed from the mandrel and the wall thickness measured with a snap gauge by placing the scaffold between two glass slides. The PGA/PLCL tubes were cut into 1.5 cm lengths and the inner diameter was 12 mm. The scaffolds were then packaged in TYVEK® pouches and terminally sterilized with gamma irradiation. The entire process id represented as flow-chart in FIGS. 7A-7F.

Mechanical Testing

Compliance and burst pressure data was acquired using a universal mechanical testing machine (MTS Systems Corporation, MN, USA). In brief, data was acquired using a load frame fitted with a 50 lb load cell with a force resolution of 10-4 pounds and a linear displacement resolution of 10-8 inches. Compliance testing was performed using a displacement velocity of 1.5 mm per minute and acquisition rate of 4 data points per second utilizing Laplace's Law (Raghavan, et al., *J Biomech.* 2000; 33:475-482; Vorp, et al., *Ann Thorac Surg.* 2003; 75:1210-1214) to correlate linear force and displacement to compliance. Burst pressure testing was performed using a displacement velocity of 50 mm per minute and acquisition rate of 4 data points/sec utilizing Laplace's Law (Raghavan, et al., *J Biomech.* 2000; 33:475-482; Vorp, et al., *Ann Thorac Surg.* 2003; 75:1210-1214) to correlate linear force and displacement to burst pressure.

Ring samples were placed around two parallel L-shaped steel rods, one rod was attached to the base of the testing machine and the other to the load cell. The samples were strained perpendicular to the length of the sample. Compliance was calculated using systolic and diastolic pressures of 120 mm Hg and 80 mm Hg, respectively. Burst pressure was calculated as the maximum pressure immediately preceding failure.

Graft Implantation

The animal care and use committee at Q-Test Laboratories (Columbus, Ohio, USA) approved the care, use, and monitoring of animals for these experiments. Six custom made cell-free nanofiber TEVGs were implanted as IVC interposition grafts in sheep (Body weight: 23.9±5.0 kg). All sheep were anesthetized with 1.5% isoflurane during surgery. The IVC was exposed and heparin (100 IU/kg) administered intravenously. The TEVG was implanted as a supradiaphragmatic IVC interposition graft using standard running 6-0 prolene suture. Two surgical clips were placed on the proximal and distal anastomoses as reference markers for angiography and necropsy. Antibiotic treatment (cefazolin) was administered intra-operatively and 7 days post-operatively. All sheep were maintained on a daily oral dose of aspirin (325 mg/day) until the 6-month end point.

Angiography

Angiography was performed to assess any potential graft complications at the 3- and 6-month time points. A 5Fr catheter was inserted into the jugular vein to the IVC, and intravenous contrast manually-injected into the supradiaphragmatic IVC and mid-graft. Additionally, the IVC blood pressure was measured at the proximal and distal anastomoses to evaluate the pressure gradients across the graft.

Histology and Immunohistochemistry

Explanted TEVG samples were fixed in 10% formalin for 24 hours at 4° C., then embedded in paraffin. For standard histology, tissue sections were stained with hematoxylin and eosin, Masson's trichrome, Picrosirius Red, Hart's, and von Kossa stains. For immunohistochemistry, tissue sections were deparaffinized, rehydrated, and blocked for endogenous peroxidase activity and nonspecific staining. The primary antibodies used included: von Willebrand Factor (1:2000, Dako), α-smooth muscle actin (1:500, Dako), myosin heavy chain (1:500, Abcam), and CD68 (1:200, Abcam). Antibody binding was detected using biotinylated secondary antibodies (Vector), followed by incubation with streptavidinated HRP (Vector). Development was performed by chromogenic reaction with 3,3-diaminobenzidine (Vector). Nuclei were counterstained with Gill's hematoxylin (Vector).

Histological and Quantitative Analysis

The lumen diameter, wall thickness, remaining scaffold area, and collagen content were measured from hematoxylin and eosin and Picrosirius red (polarized light) stainings using Image J software (National Institutes of Health, Bethesda, Md., USA). Picrosirius red staining revealed collagen fibers (Lattouf, et al., *J Histochem Cytochem.* 2014; 62:751-758). CD68+ macrophages were quantified by analyzing four high powered fields (HPF, 40×) from a representative section of each sample (n=6) and averaged.

Biochemical Analysis

Elastin content was determined using a Fastin colorimetric assay (Biocolor Assay, Inc). 100 mg dry weight of each sample was measured and transferred to 1.5 ml microcentrifuge tubes containing 750 μl 0.25 M oxalic acid. The tubes were then placed on a heat block for 60 min at 100 degree Celsius to convert insoluble elastin to water-soluble α-elastin. The elastin content in each sample was determined by detection at 513 nm and interpolation to a standard curve after precipitation and dye binding following the manufacturer's protocol. Collagen content was determined by a Sircol colorimetric assay (Biocolor Assay, Inc). 100 mg dry weight of each sample was measured and transferred to low protein binding 1.5 ml conical microcentrifuge tubes containing 1.0 ml of pepsin (Sigma-Aldrich), with a concentration of 0.1 mg/ml of 0.5 M acetic acid to solubilize the collagen by means of overnight incubation. The collagen content in each sample was determined by detection at 555 nm and interpolation to a standard curve after precipitation and dye binding following the manufacturer's protocol Statistics For all experiments, data are represented graphically as scatter plots of individual values with a bar identifying the median, manuscript references are mean±standard deviation. Burst pressure, compliance, and outer diameter change data were analyzed via one-way ANOVA with Tukey's multiple comparisons test. Pressure gradient data was analyzed by a paired two-tailed t-test. Analysis of elastin, collagen, collagen area %, and wall thickness data was performed with unpaired two-tailed t-test. To determine the significance of any correlation between wall thickness and CD68+ macrophages/HPF the Pearson correlation coefficient was calculated. $p<0.05$ was considered statistically significant. Statistical analysis was performed using Graphpad Prism (GraphPad Software, Inc., version 6, CA, USA).

Results

All sheep survived without complications, and all grafts were patent without aneurysm formation or ectopic calcification. Serial angiography revealed significant decreases in TEVG pressure gradients between 3 and 6 months as the grafts remodeled. At explant, the nanofiber scaffold was nearly completely resorbed and the TEVG showed similar mechanical properties to that of native IVC. Histological analysis demonstrated an organized smooth muscle cell layer, extracellular matrix deposition, and endothelialization. No significant difference in elastin and collagen content between the TEVG and native IVC was identified. There was a significant positive correlation between wall thickness and CD68+macrophage infiltration into the TEVG.

Mechanical Properties of Patient-Specific Cell-Free Nanofiber TEVG

Electrospinning created a tubular scaffold with a uniform wall thickness of 657 μm±36 μm which is significantly less than the native IVC wall thickness of 1365±476 μm.

Figure 8A:
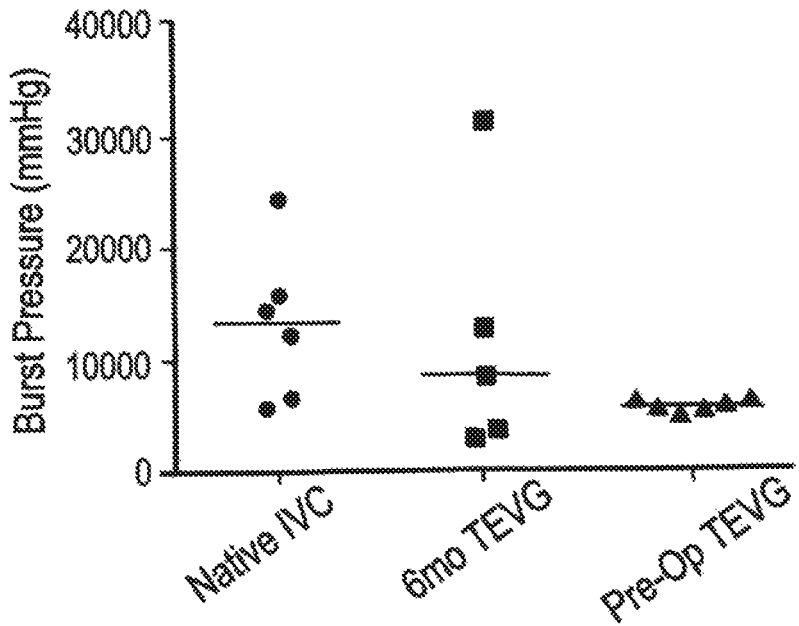
FIG. 8A is a histogram showing Burst Pressure (mmHg 0-40,000) for each of Native IVC (●), 6 mo TEVG (■), and Pre-Op TEVG (▲) samples, respectively.
Figure 8B:
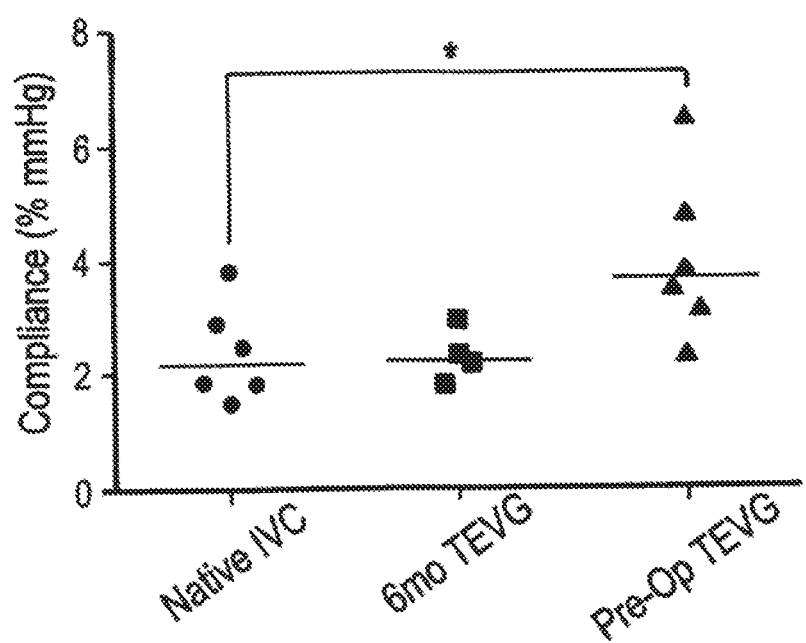
FIG. 8B is a histogram showing Compliance (0-8% mmHg) for each of Native IVC (●), 6 mo TEVG (■), and Pre-Op TEVG (▲) samples, respectively (* p<0.05).

There was no significant difference in the burst pressure of the graft prior to implantation when compared to the native IVC; similarly, no significant difference in burst pressure was observed between the native IVC and the TEVG at 6 months (FIG. 8A; Native IVC: 13062±6847 vs. 6-month TEVG: 11685±11506 vs. Pre-op TEVG: 6167±5627 mmHg; p=0.22). The pre-operative graft compliance was significantly higher when compared to the native IVC (FIG. 3B; Pre-Op TEVG: 4.0±1.5 vs. Native IVC: 2.4±0.85%; p<0.05). However, there was no significant difference in compliance between the native IVC and TEVG after 6 months (FIG. 8B, Native IVC: 2.4±0.85 vs. 6-month TEVG: 2.3±0.46%; p >0.05).

Biocompatibility in High-Flow Low-Pressure Venous Circulation

Figure 9A:
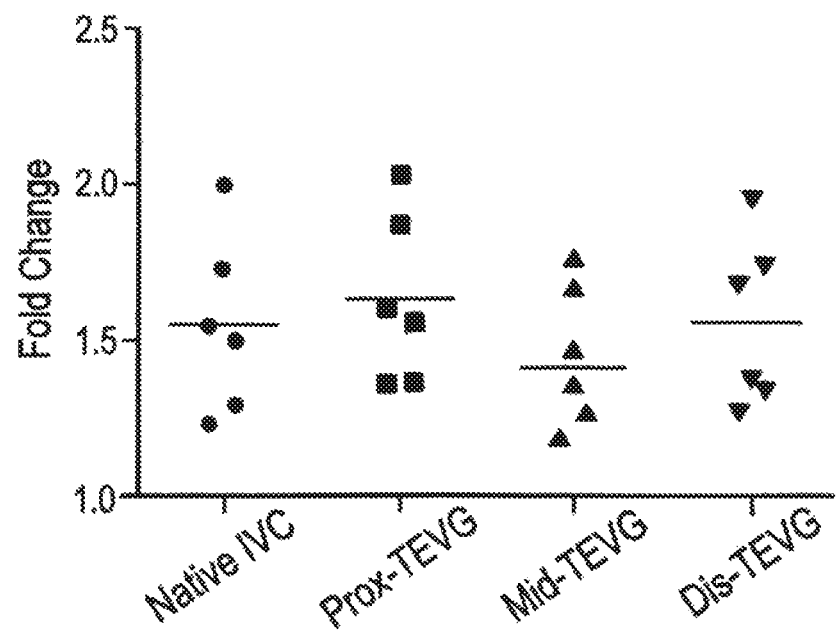
FIGS. 9A-9D are graphs.
Figure 9B:
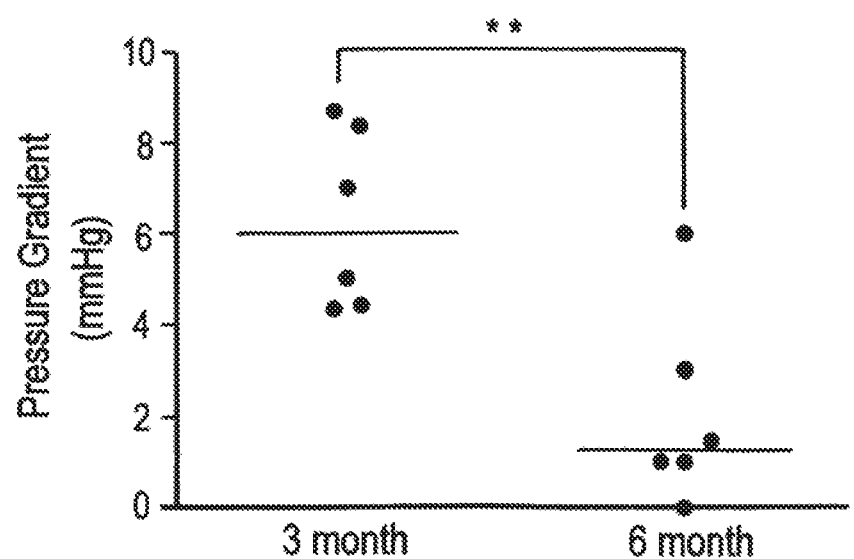

Graft biocompatibility including patency and tissue remodeling was excellent within the 6-month study duration. All sheep survived until the study end point without any graft-related complications, such as stenosis, dilation, or rupture. Native IVC and the patient-specific TEVG were evaluated at 3 and 6 months for evidence of stenosis or dilation with contrast enhanced angiography. There was no significant difference in the fold change of measured lumen diameters between 3 and 6 months when comparing the native IVC to the proximal, middle, or distal regions of the TEVGs. Both the IVC and patient-specific TEVG displayed no significant diameter changes between the 3- and 6-month time points (FIG. 9A). The pressure gradient across the TEVG at 6 months was significantly less than at 3 months, suggesting advantageous remodeling and scaffold degradation (FIG. 9B, 3 month: 6.3±2.0 vs, 6 month: 2.1±2.2 mmHg, p=0.0045).

Figure 9C:
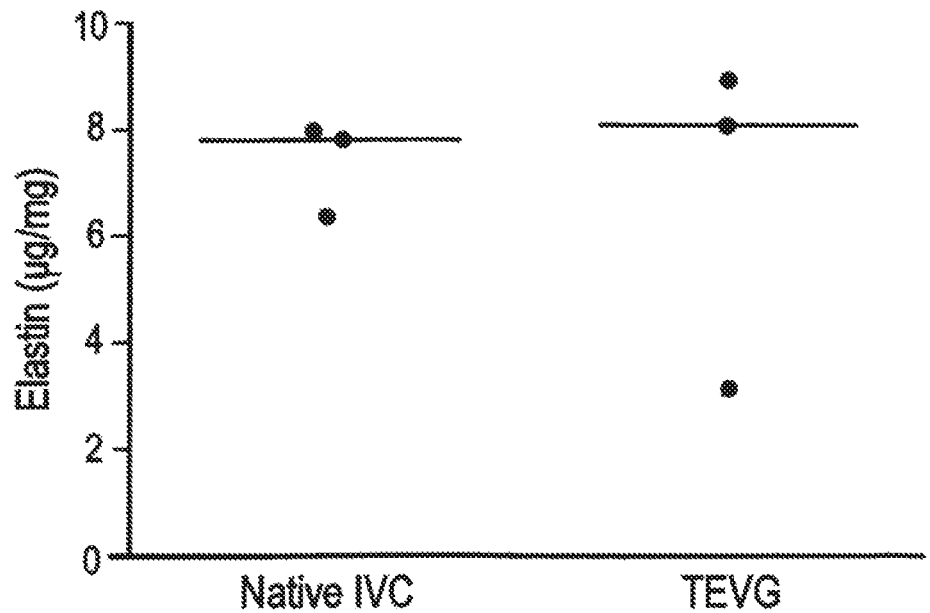
Figure 9D:
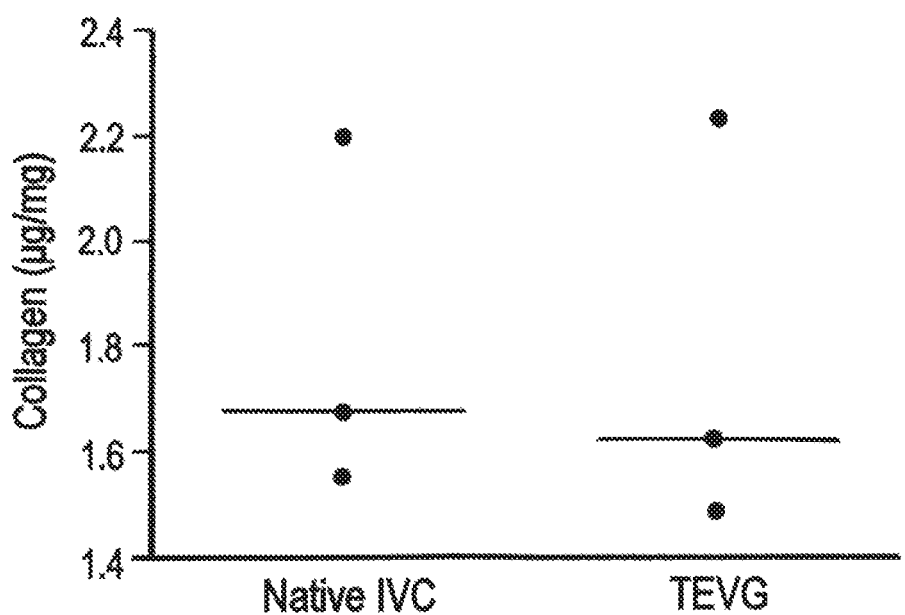

Elastin and collagen are critical for venous function and are well-studied markers of vascular graft remodeling. Biochemical quantification revealed the TEVG's elastin content (FIG. 9C, 6.7±3.1 vs. 7.4 0.88 μg/mg, p=0.74) and collagen content (FIG. 9D, 1.8±0.4 vs. 1.8±0.35 μg/mg, p=0.93) were equivalent to that of the native ovine IVC.

Well-Organized Vascular Neotissue Formation

The tailor-made nanofiber TEVG demonstrated well-organized vascular neotissue formation over 6 months. Hematoxylin and eosin staining demonstrated extensive cellular infiltration into the TEVG, evidence that scaffold parameters such as pore size and fiber diameter permitted host cell infiltration. All cell-free TEVGs remained patent without complications. Importantly, hematoxylin and eosin staining visualized under polarized light microscopy revealed that only 2.09±0.69% of the nanofiber scaffold material remained at 6 months, indicating that the vascular neotissue was the primary contributor to the biochemical and mechanical properties assessed, further supporting the safety and efficacy of this approach. Furthermore, in vitro studies (data not shown) demonstrate that the TEVG loses all mechanical strength after 12 weeks.

On the graft's luminal surface, a cellular monolayer stained positively for von Willebrand Factor confirming successful endothelialization like native tissue. The luminal surfaces displayed no evidence of microthrombosis.

Figure 10:
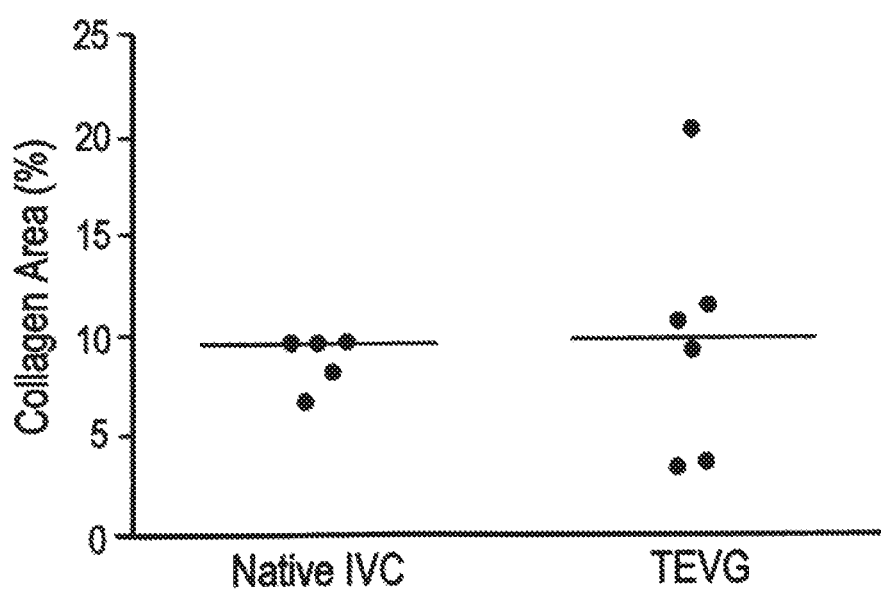
FIG. 10 is a graph showing Collagen Area (%) for samples of Native IVC, and TEVG, respectively.

Smooth muscle cells are important for vascular function and we identified mature contractile vascular SMCs using α-smooth muscle actin and myosin heavy chain markers at 6 months in the TEVG. A layer of myosin heavy chain positive cells was circumferentially organized and maintained adequate wall thickness at subintimal layers. A multilayered population of α-smooth muscle actin positive cells was primarily present in the neomedia, suggesting that the TEVG may not have been a completely mature neo-IVC at 6 months and that active vascular remodeling was still occurring at this time point. Alternatively, α-smooth muscle actin could indicate synthetic SMCs or myofibroblasts, and the α-smooth muscle actin+/myosin heavy chain-staining observed in the TEVG may identify the neo-adventitia or areas of continued growth and remodeling. Extracellular matrix constituents in the TEVG mimicked the circumferential orientation observed in the native IVC. The extracellular matrix density in the TEVG (stained with Picrosirius red, F: Masson's trichrome) resembled that of native tissue. Collagen deposition, organization, and maturation were confirmed by assessing relative amounts and orientation of thin and thick fibers. The Picrosirius red staining showed that the area fraction of collagen was similar in both the TEVG and native IVC (FIG. 10, 9.75±6.27 vs. 8.75±1.31%, p=0.74). Hart's staining demonstrated that the elastin composition of the TEVG was comparable to that of the native IVC. There was no evidence of ectopic calcification in von Kossa staining at 6 months.

Figure 11A:
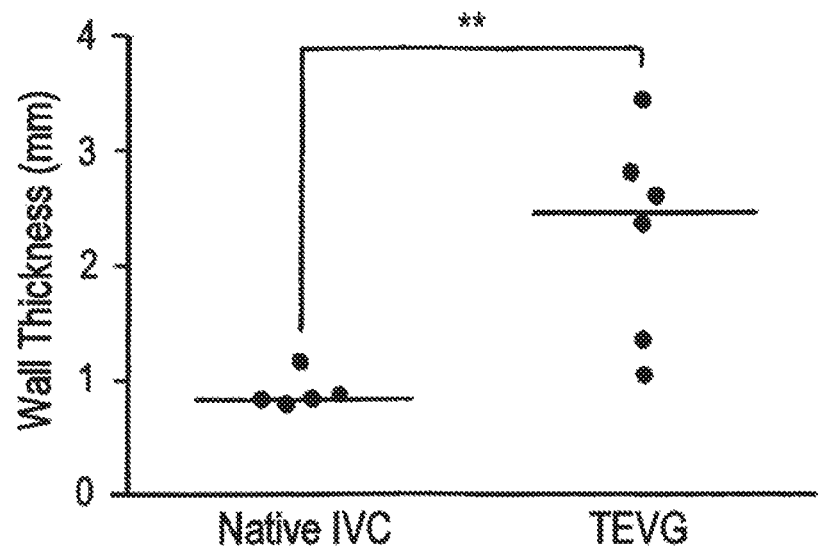
FIGS. 11A-11B are graphs.
Figure 11B:
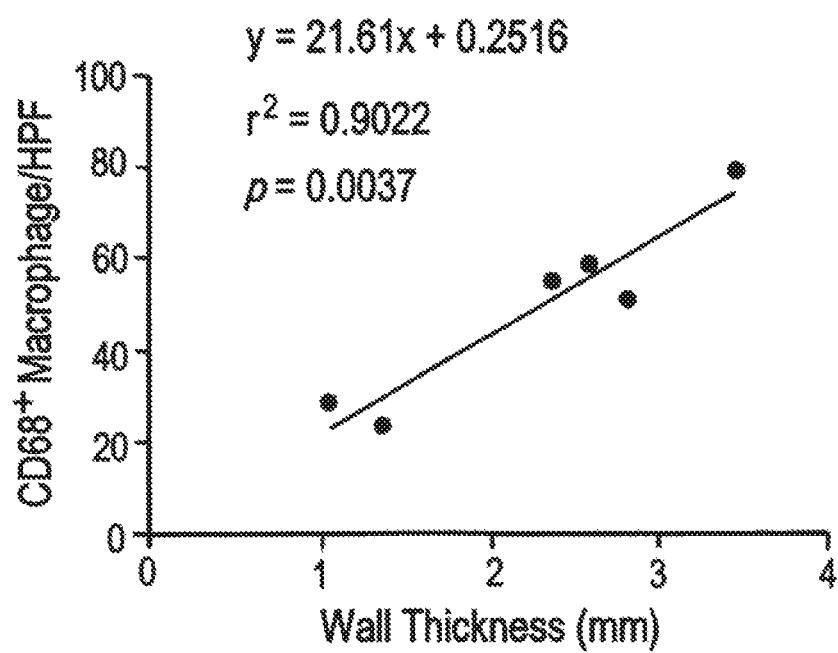

The wall thickness of the TEVG was significantly larger than that of native IVC (FIG. 11A, TEVG (N=6): 2.27±0.91 mm vs. Native IVC (N=5): 0.89±0.15 mm, p=0.0091). There was a significant positive correlation between TEVG wall thickness and macrophage infiltration into the scaffold (FIG. 11B, two-tailed Pearson correlation, p=0.0037, R2=0.90), suggesting that CD68+ macrophages induced the inflammatory process of vascular remodeling in the graft which resulted in an increased wall thickness of the TEVG (FIG. 11B).

Discussion

The results of this study validate the efficacy of patient-specific, cell-free nanofiber TEVGs created by computer aided design modeling, 3D-printing, and electrospinning. The patient-specific TEVG was comparable to a native IVC in terms of mechanical properties, angiography, histology, and immunohistochemistry. Serial angiography revealed that the initial pressure gradients between the cell-free, patient-specific TEVG and native IVC gradually resolved during the study's 6 month-time course as the polymer scaffold was resorbed. Additionally, the mechanical profile of the TEVG resembled that of the native IVC by the study end point.

It is becoming more commonplace that advances in 3D-printing technologies are being integrated with the fields of regenerative and translational medicine to create novel solutions to challenges in tissue engineering. One such example is the clinical use and development of a 3D-printed biodegradable tracheal splint. However, the relevance of 3D-printing technologies in clinical applications of TEVGs has been limited due to a lack of suitable materials that can be 3D-printed. Recent studies have focused on fully synthetic biodegradable polymers or synthetic polymers blended with natural proteins such as collagen, elastin, gelatin, and chitosan. Although more current bio-printing efforts have produced biological blood vessels, the construct's mechanical properties are insufficient unless the tissue is further cultured for maturation.

Previous studies have also examined TEVG fabrication utilizing solvent-cast molding processes with synthetic biodegradable polymers, but 3D-printing TEVG scaffolds would best streamline the process of creating a patient-specific conduit. The functionality of a 3D-printed TEVG scaffold in a mouse model was also investigated. The TEVG was an unseeded, cell-free construct and possessed adequate mechanical properties capable of supporting vascular tissue growth both in vitro and in vivo (Melchiorri, et al., *Adv Healthc Mater.* 2015). The 3D-printed TEVGs were implanted as IVC conduits in immunocompromised mice and demonstrated biocompatibility and long-term efficacy 1 year post-op, however, the degradation rate of this scaffold (poly(propylene fumarate)) was suboptimal. FDA approved materials with a known degradation profile, a 3D-printed mandrel, and electrospinning were used to produce custom TEVGs that could be easily translated to the clinic. Electrospinning is advantageous in that it is a highly tunable process by which a wide variety of polymer types and fiber sizes can be spun into various shape of mandrels, thus allowing for the rational design of custom made scaffolds for tissue engineering (Rocco, et al., *Tissue Eng Part B Rev.* 2014; 20:628-640).

The current "one-size-fits-all" paradigm inadequately addresses the variable and complex anatomies present in the congenital heart disease population. Patient-specific TEVGs are useful for patients with SVAs who undergo extra-cardiac TCPC. Clinical studies have demonstrated the geometry of the TCPC plays a key factor in energy losses by suboptimal hepatic flow distribution. Additionally, advances in computational models have led to the development of more physiologically realistic patient-specific simulations (de Zelicourt, et al., *Prog Pediatr Cardiol.* 2010; 30:31-44). Computational modeling has indicated that TCPC energy loss inversely correlates with decreased diameter of the TCPC conduit and pulmonary artery. These simulations also found hepatic flow distribution to correlate with caval offset, pulmonary flow distribution, and the connection angle between the TCPC and SVC (Tang, et al., *JACC Cardiovasc Imaging.* 2014; 7:215-224). Further studies have examined Y-Fontan grafts to avoid flow collision from the SVC and IVC and promote equally distributed hepatic flow to the lungs (Restrepo, et al., *Ann Thorac Surg.* 2016; 101:183-189).

The nanofiber construct described herein promotes autologous vessel growth, overcoming concerns associated with more rigid materials, such as flow and diameter mismatch. Patient-specific grafts can also avoid the need to offset SVC positioning in patients with limited implantation space due to anatomical restrictions. Therefore, the patient-specific TEVG, by taking advantage of recent advances in imaging and computational modeling, should provide improved clinical and surgical outcomes.

Although the use of PLCL and PGA as the choice of synthetic biodegradable materials led to effective graft mechanical properties and remodeling in the previous human trial, second-generation electrospun PGA/PLCL scaffold designs with optimized nanofiber parameters are now being tested.

The patient-specific nanofiber TEVG displayed satisfactory vascular remodeling at 6 months post-op. In comparison to the native IVC, the TEVG at 6 months displayed a significantly thicker layer of SMCs. Angiography showed the pressure gradients of the TEVG at 6 months was significantly lower than at 3 months. Additionally, there was no significant difference at 6 months between the TEVG and native IVC with regards to burst pressure and compliance. A well-organized vascular smooth muscle cell layer is required to prevent vascular calcification, but excessive smooth muscle cell proliferation may eventually lead to stenosis or complete occlusion due to hyperplasia. Due to the 6-month time course of this study, it is difficult to ascertain whether the vascular smooth muscle cell layer that developed in the TEVG would eventually resemble native IVC or progress to become occlusive stenosis at later time points.

A significant positive correlation between TEVG wall thickness and CD68+macrophage infiltration into the scaffold. It was previously reported that a scaffold seeded with bone marrow mononuclear cells transforms into a living vascular conduit with the ability to grow, repair, and remodel via an inflammation mediated process (Roh, et al., *Proc Natl Acad Sci USA*. 2010; 107:4669-4674). Additionally, previous studies suggested that excessive macrophage infiltration contributes to occlusive vascular neotissue hyperplasia (Hibino, et al. *FASEB J.* 2011; 25:2731-2739; Hibino, et al. *FASEB J.* 2015; 29:2431-2438). When compared to the native IVC, the TEVG's wall thickness was thicker, which may indicate the progression of chronic intimal hyperplasia.

We claim:

1. A patient-specific tissue engineerable biodegradable polymeric vascular graft or conduit comprising nanofibers of electrospun polymer, wherein the polymer is selected from the group consisting of poly(lactic acid-glycolic acid), poly (lactic acid), poly(glycolic acid) and poly(caprolactone),
    wherein the graft or conduit comprises pores between 5 and 500 microns in diameter allowing infiltration of cells as the polymer degrades,
    wherein the graft or conduit conforms to a variable and complex geometry of an artery or vein within a patient.

2. The patient-specific polymeric vascular graft or conduit of claim 1, formed on a mandrel conforming to the patient's anatomy at the site of implantation.

3. The patient-specific polymeric vascular graft or conduit of claim 1 comprising an effective amount of viable cells on the patient-specific polymeric vascular graft or conduit to reduce or prevent post-operative stenosis of the graft relative to the graft without the cells prior to implantation.

4. The patient-specific polymeric vascular graft or conduit of claim 1, having attached thereto an amount of viable cells between about $0.5 \times 10^3$ cells/mm$^2$ graft and $300 \times 10^3$ cells/mm$^2$ graft, inclusive.

5. The patient-specific polymeric vascular graft or conduit of claim 1, wherein the graft has attached thereto an amount of viable cells between about $1.0 \times 10^3$ cells/mm$^2$ graft and $100 \times 10^3$ cells/mm$^2$ graft, inclusive.

6. The patient-specific polymeric vascular graft or conduit of claim 3, wherein the viable cells are autologous cells.

7. The patient-specific polymeric vascular graft or conduit of claim 3, wherein the viable cells are bone marrow mononuclear cells.

8. The patient-specific vascular graft or conduit of claim 1, wherein the graft further comprises one or more additional agents selected from the group consisting of anti-neointima agents, chemotherapeutic agents, steroidal and non-steroidal anti-inflammatories, conventional immunotherapeutic agents, immune-suppressants, cytokines, chemokines, and growth factors.

9. The patient-specific polymeric vascular graft or conduit of claim 1, wherein the graft is created by a method comprising the steps of
    (a) computer aided design modeling of graft morphology;
    (b) 3D-printing of a mandrel model of the graft or conduit; and
    (c) forming the graft or conduit based on the morphology of the mandrel.

10. The patient-specific polymeric vascular graft or conduit of claim 9, comprising cells thereon wherein
    the number of cells used to contact the graft is proportional to the surface area of the graft, and is between about $1.0 \times 10^4$ cells/mm$^2$ graft and $500 \times 10^6$ cells/mm$^2$ graft.

11. The patient-specific polymeric vascular graft or conduit of claim 10, wherein the graft is contacted with an amount of cells between $0.5 \times 10^6$ cells and $100 \times 10^6$ cells.

12. The patient-specific polymeric vascular graft or conduit of claim 9, wherein the graft is contacted with cells for less than 3 hours, in a sterile, closed seeding chamber.

13. The method of claim 12, wherein the graft is contacted with cells for less than one hour.

14. A method of seeding viable cells onto the graft of claim 3, the method comprising using a sterile chamber comprising a suction rod and vacuum-assisted seeding to seed the viable cells onto the graft in the chamber.

15. The method of claim 14, wherein the graft is placed over the mandrel, and a mandrel is placed over the suction rod in the sterile chamber.

16. The method of claim 14, wherein the viable cells are autologous cells obtained from patient's biological material.

17. The method of claim 16, wherein a portion of the biological material is transferred back to the patient.

18. The method of claim 17, wherein the portion of the biological material that is transferred back to the patient is selected from the group consisting of plasma, red blood cells, platelets, white blood cells and combinations thereof.

19. The method of claim 14, wherein seeding of the viable cells onto the graft comprises incubating the graft with the viable cells in the sterile chamber.

20. The method of claim 19, wherein incubating is for a period of time of less than 2 hours.

21. The method of claim 19, wherein incubating is for a period of time of less than one hour.

22. The patient-specific polymeric vascular graft or conduit of claim 9, wherein contacting the graft with cells is contacting in a sterile seeding chamber.

* * * * *